United States Patent [19]

Amano

[11] Patent Number: 5,437,634
[45] Date of Patent: Aug. 1, 1995

[54] MEDICAL PUMP DRIVING DEVICE

[75] Inventor: Nobuhiko Amano, Kanagawa, Japan

[73] Assignee: Terumo Kabushiki Kaisha, Tokyo, Japan

[21] Appl. No.: 51,567

[22] Filed: Apr. 22, 1993

Related U.S. Application Data

[63] Continuation-in-part of Ser. No. 963,859, Oct. 20, 1992, abandoned.

[51] Int. Cl.$^6$ ............................................. A61M 5/00
[52] U.S. Cl. ..................................................... 604/65
[58] Field of Search ...................... 604/65, 67, 30, 31, 604/50, 66, 250, 251, 253, 256; 128/DIG. 12–DIG. 13

[56] References Cited

U.S. PATENT DOCUMENTS 4,401,431 8/1983 Arp .
4,840,620 6/1989 Kobayashi et al. .

FOREIGN PATENT DOCUMENTS 2-0228160 7/1987 European Pat. Off. .
2-0357338 3/1990 European Pat. Off. .

Primary Examiner—C. Fred Rosenbaum
Assistant Examiner—Manuel Mendez
Attorney, Agent, or Firm—Frishauf, Holtz, Goodman & Woodward

[57] ABSTRACT

A medical pump driving device comprises a centrifugal pump for transferring liquid in a liquid channel including an artificial lung, a motor for driving the centrifugal pump, and a bubble removing mechanism for removing a bubble from the liquid channel including the medical device by transferring liquid by the pump. The bubble removing mechanism comprises a CPU for setting various types of set values to intermittently drive the motor, a RAM and an EEPROM for storing the set value set by the CPU, an D/A converter 251, and motor driving circuit for intermittently driving the motor based on the set value stored in the RAM, and EEPROM.

18 Claims, 16 Drawing Sheets

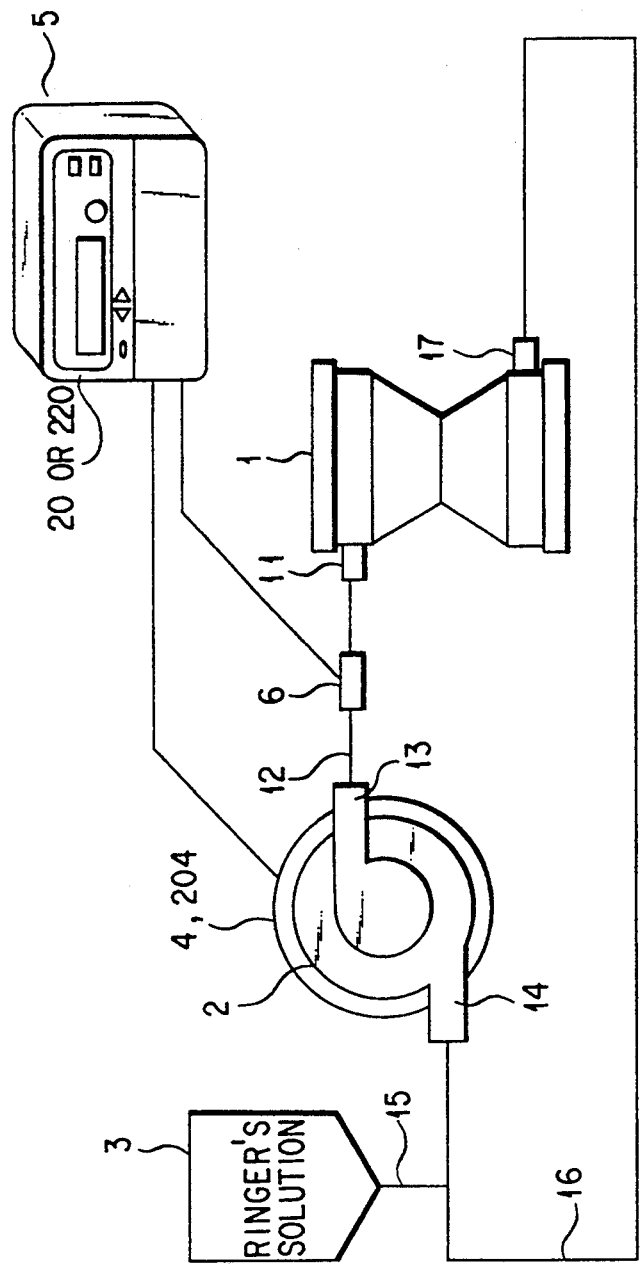
F I G. 1

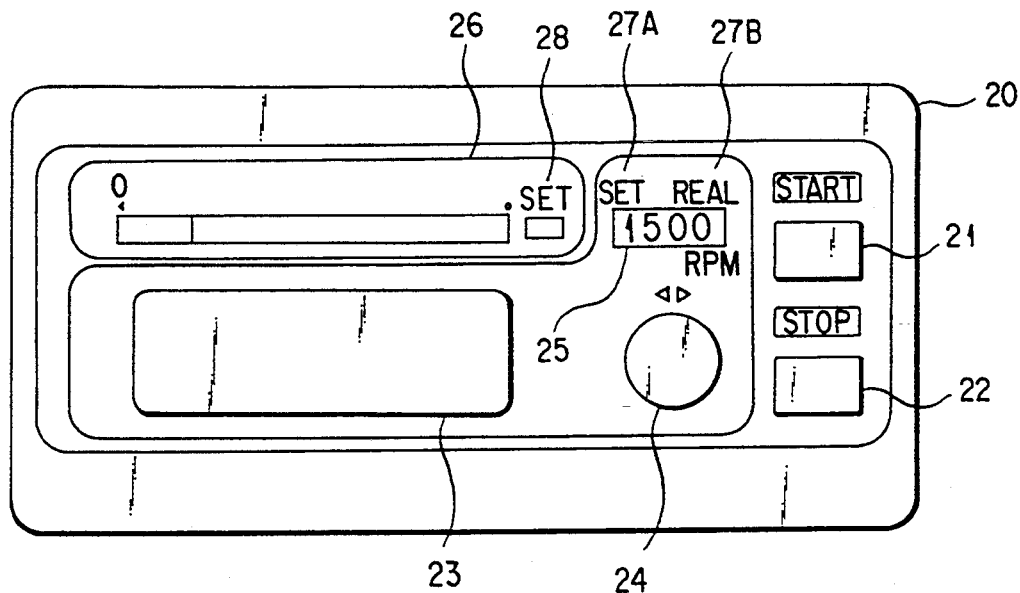
F I G. 2
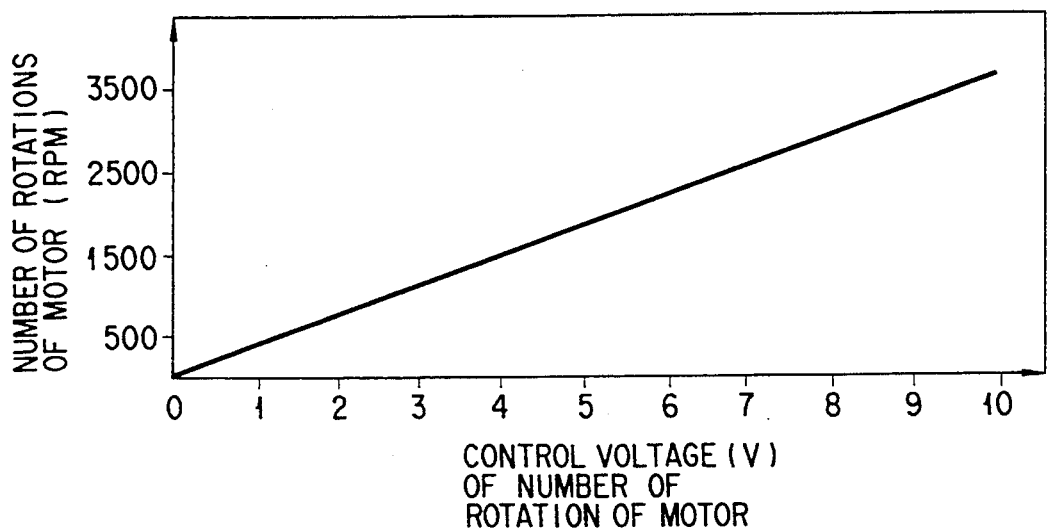
F I G. 4

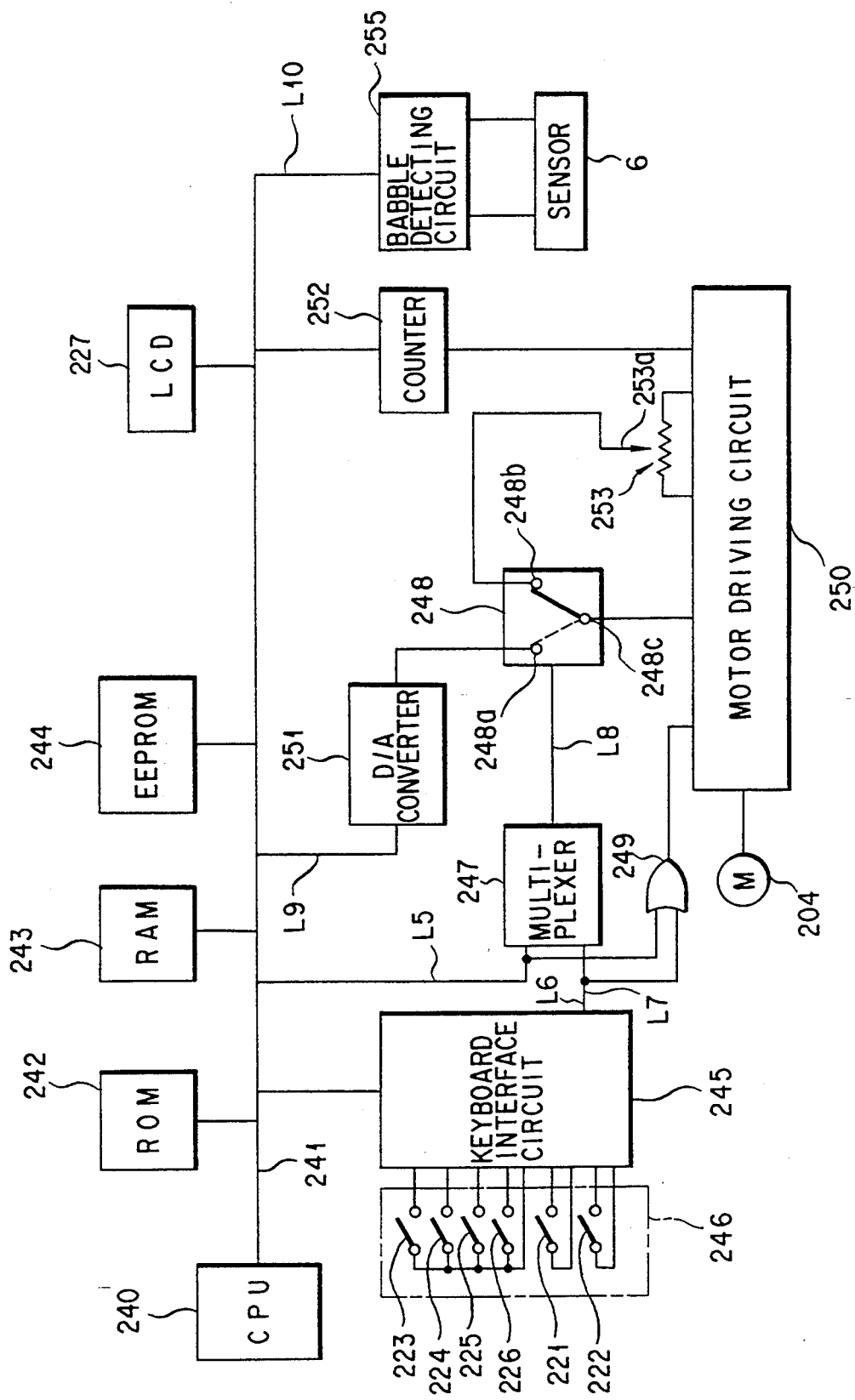
F I G. 6

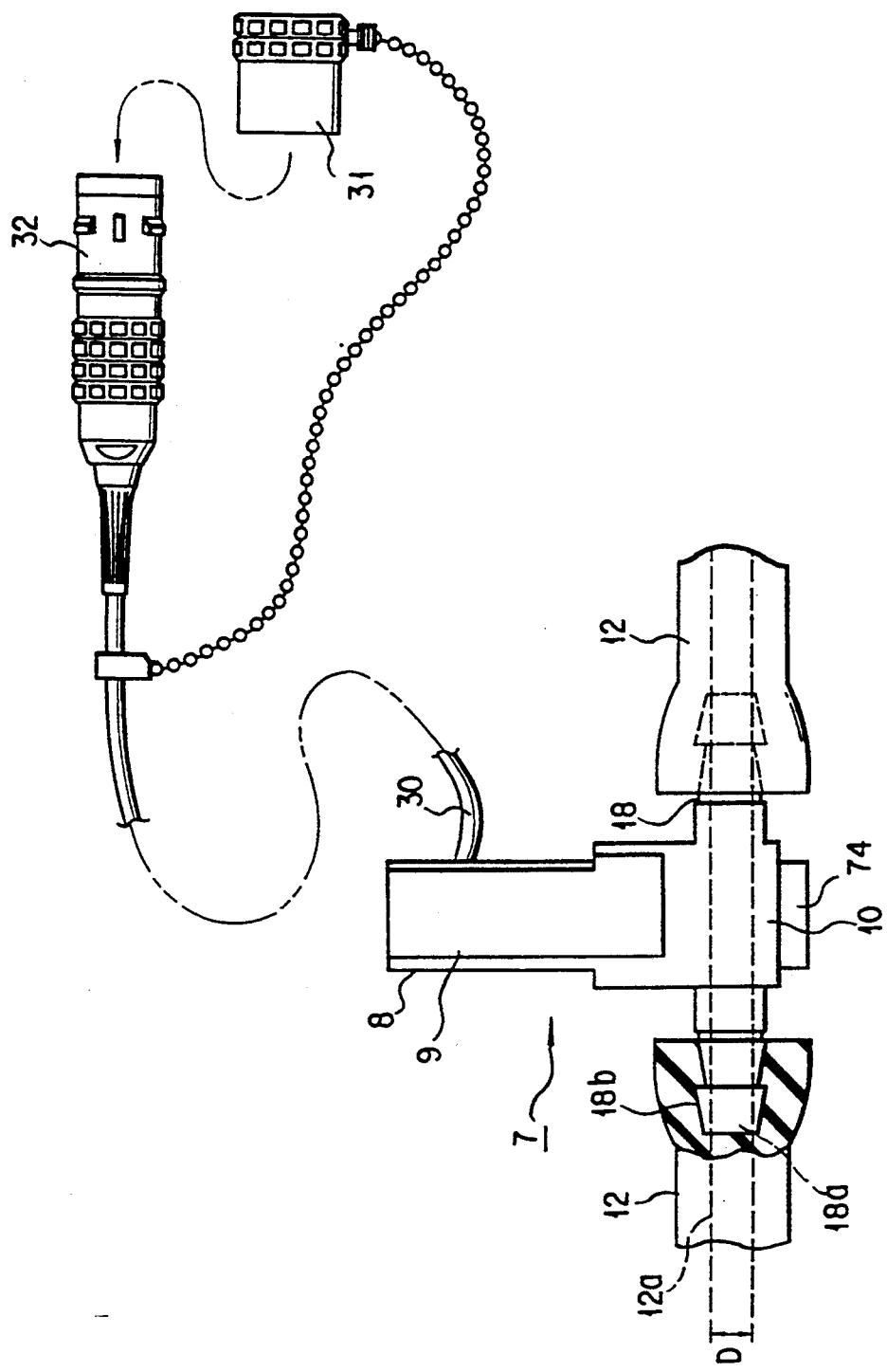
F I G. 13

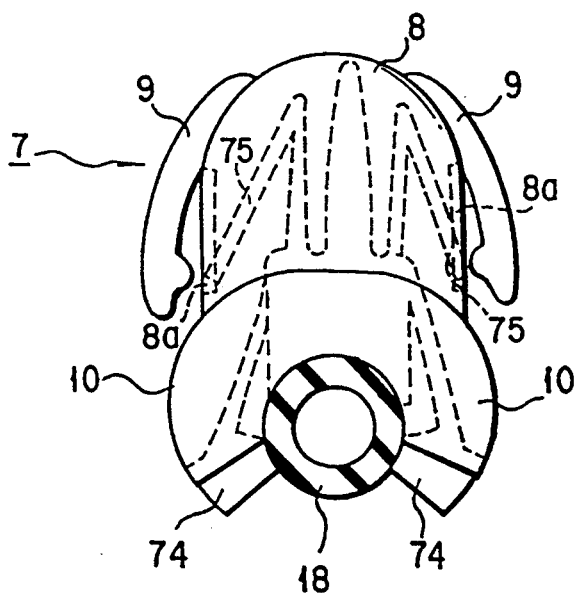
F I G. 14
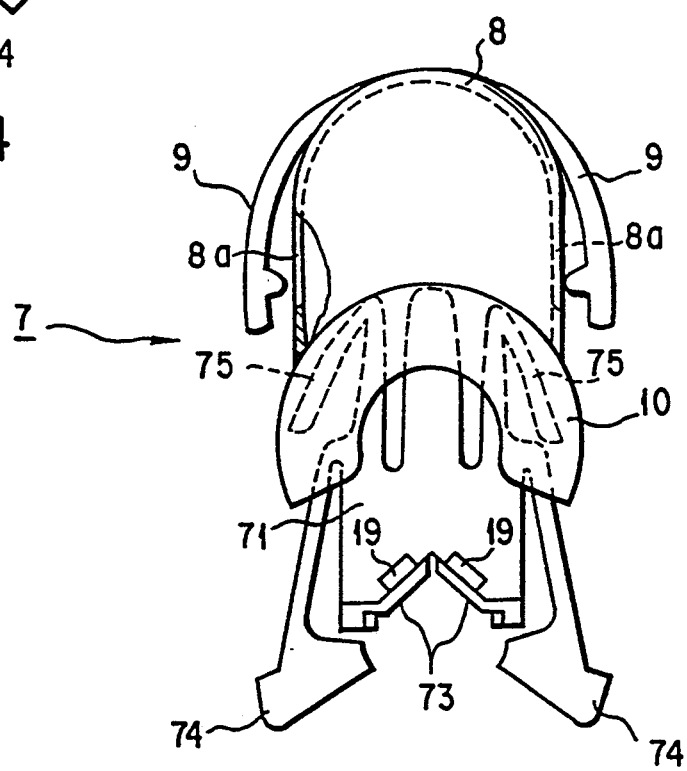
F I G. 15
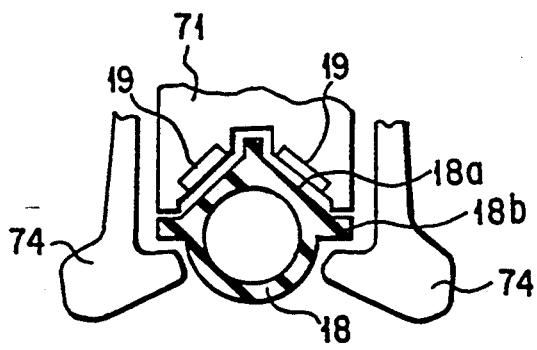
F I G. 16

MEDICAL PUMP DRIVING DEVICE

This application is a continuation-in-part of application Ser. No. 07/963,859, filed Oct. 20, 1992 now abandoned.

BACKGROUND OF THE INVENTION

1. Field of the Invention

The present invention relates to a medical pump driving device and, more particularly to a medical pump driving device having a function of setting the number of rotations of the medical pump, and display means for displaying the set value of the number of rotations. The present invention also relates to a medical pump driving device which removes bubble existing in a liquid channel including a medical pump and the other medical devices. Further, the present invention also relates a medical pump driving device having a sensor unit for obtaining flow rates of liquids such as blood.

2. Description of the Related Art

Generally, in an external circulation using a medical device for artificial lungs and the like or an auxiliary circulation, a medical pump such as a centrifugal pump is used as means for transferring liquid such as blood or Ringer's solution.

In case that liquid is transferred to a human body by the medical pump, the number of rotations of the pump is set in advance before a beginning of the pump driving. Since liquid flow rate is substantially proportional to the number of rotations of the pump, the number of rotations of the pump is set by rotating a dial on an operation panel. In other words, an operator obtains the number of rotations of the pump corresponding to the liquid flow rate at the time of operation, and adjusts a scale of the dial to the obtained number of rotations of the pump. Normally, by the the operator, the dial is made one rotation or 10 or more rotations for obtaining accuracy.

However, in the conventional pump driving device, the number of rotations i.e. rounds per minute (r.p.m) of pump is not displayed on the panel until the pump is actually driven. Due to this, if the pump driving is begun without preparation, liquid is intensively transferred by depending on the set value (the value of the dial scale corresponding to the predetermined number of rotations of the pump). Particularly, in the external circulation using the artificial lungs, if blood is intensively transferred to the human body, a patient often falls into a dangerous state. Therefore, for safety, the operator once returns the dial to a minimum of the scale, thereafter the pump driving is begun, and the dial is rotated little by little so as to gradually increase the number of rotations of the pump. Then, the scale of the dial is set at the set value, and finally reached to the predetermined number of rotations of the pump.

As mentioned above, in the conventional device, the operator must monitor the dial scale during the operation, the operation is complicated, and an excessive load is forcibly imposed on the operator. Moreover, in case that the centrifugal pump is used and the number of rotations is small, there is danger that blood will flow backward.

There is a case that the medical device for the artificial lungs is connected to the medical pump and the auxiliary circulation is performed. In the auxiliary circulation, if bubble exists in the blood channel, a serious trouble occurs. Particularly, the operation for removing bubble from the blood channel of an external circulation circuit of the artificial circuit is extremely important. This is because a large number of hollow fiber membranes and complex and narrow channels such as a tube and a connector, and the like are provided in the blood channel of the external circulation circuit of the artificial lung.

Due to this, a so-called priming operation is performed before the auxiliary circulation. The priming operation is that the blood channel is filled with Ringer's solution, and that bubble is removed therefrom. In general, in the priming operation, vibration is applied to the blood channel as the pump is driven at a constant speed, thereby removing bubble from the inner wall of the channel.

However, great skill is required to the operator so as to perform such the priming operation. Also, a long period of time is needed to perform the priming time. Therefore, the operator cannot freely leave the operation panel, and the operator's movement is restricted.

In recent years, attention has been paid to EBS circulation is manually performed on the spot in a situation that the external circulation circuit of the artificial lungs must be used in the patient at once. In the auxiliary circulation, blood is bled from a femoral vein of the patient, and passed through the artificial lungs. Thereafter, blood is returned from a femoral artery. However, since the conventional priming operation is complicated and needs much time, this generates a big trouble in performing EBS, which needs emergency. Recently, a centrifugal pump has often been used as a means for externally or auxiliarily circulate liquids such as blood and Ringer's solution into the human body while using medical devices such as an artificial lung. This centrifugal pump is characterized in that the amount of liquid pumped out by the pump changes depending upon after-load and change of pressure in the liquid-circulating channel or circuit. In order to accurately control the amount of liquid circulated responsive to any change in the amount of liquid pumped out by the centrifugal pump, it is necessary to accurately know the flow rate of liquid or blood in the liquid-circulating circuit. A sensor is therefore attached to a liquid- or blood-circulating tube which forms the liquid-circulating circuit to measure the flow rate of the liquid flowing in the circuit.

The flow rate sensor is usually connected to the input section of the pump drive unit and when a detection (or flow velocity) signal is applied to the input section, the flow rate is arithmetically calculated responsive to this applied signal. Electro-magnetic and ultrasonic sensors which use electro-magnetic force and ultrasonic wave can be used as the sensor of this type. In the case of a electromagnetic flow meter (or sensor), however, calibration must be conducted before the flow meter is made operative. Until the flow meter can be made ready for operation, therefore, it takes time and it is also troublesome.

The ultrasonic sensor is therefore usually used to measure the flow rate of a liquid in the liquid-circulating circuit of the medical pump driving device. In the case of the conventional ultrasonic sensor, the flow velocity of the liquid is measured and this flow velocity thus measured is converted into the flow rate. When liquid or blood is to be externally or auxiliarily circulated into the human body through the liquid-circulating circuit or channel, therefore, data relating to the inner diameter of the liquid-circulating circuit or tube must be stored, for every sensor, in the memory of a CPU. In addition, flow velocity values measured by sensor units may not be accurate because the sensor units are not necessarily attached to the liquid-circulating tube in same manner. In order to correct these irregular measured flow velocity values, an identifying number must be inputted into the CPU every time a sensor unit is exchanged with another one. This is time consuming and troublesome.

SUMMARY OF THE INVENTION

It is an object of the present invention is to provide a medical pump driving device which can remove bubble from a liquid channel passing through a medical pump, an artificial lungs, a tube, and the like without a complicated operation for a short period of time.

Moreover, it is another object of the present invention to provide a medical pump driving device which an operator can safely operate without operating the adjustment of a dial scale on an operation panel.

A further object of the present invention is to provide a medical pump driving device capable of making it unnecessary for the operator to input a large number of data into the CPU, automatically correcting irregular measured flow velocity values, and making the liquid-circulating channel or circuit, through which liquid is externally or auxiliarily circulated into the human body, ready for operation in a shorter time.

The medical pump driving device of the present invention comprises pump means for transferring liquid in a liquid channel including a medical device, motor means for driving the pump means, and bubble removing means for removing a bubble from the liquid channel including the medical device by transferring liquid by the pump means. The bubble removing means comprises setting means for setting various types of set values to intermittently drive the motor means, set value storing means for storing the set value set by the setting means, and intermittent drive control means for intermittently driving the motor means based on the set value stored in the set value storing means.

According to the above-structured medical pump driving device, the pump means is intermittently driven by the motor means based on the various types of set values stored in the storing means. Therefore, the bubble in the liquid channel can be automatically and efficiently removed therefrom for a short period of time.

Moreover, the medical pump driving device of the present invention further comprises constant speed driving control means for driving the motor means at a constant speed, and mode changing means for changing a first mode by the constant speed drive control means and a second mode by the intermittent drive control means.

According to the above-structured medical pump driving means, the first mode in which the pump means is driven at a constant speed and the second mode in which the second mode in which the pump means is intermittently driven can be arbitrarily set. Therefore, in the case that the operator determines that no intermittent drive is needed, the constant drive can be easily selected.

Moreover, priority order setting means for setting the first mode prior to the second mode may be provided.

Furthermore, bubble detecting means for detecting bubble in the liquid channel may be structured such that the intermittent control means controls the intermittent drive of the motor means based on the output of the bubble detecting means. Thereby, the bubble removing operation can be efficiently performed.

Moreover, display means for displaying the set value stored in the set value storing means may be provided. Thereby, the operator can change various set values on an interactive basis.

According to an aspect of the present invention, a medical pump driving device comprises pump means for transferring liquid in a liquid channel including a medical device, motor means for driving the pump, dial means for adjusting the number of rotations of the motor means, an operating unit operating the dial means, first display means for displaying the number of rotations set by operating the dial means by the operation unit when the pump means is stopped, real number of rotations detecting means for detecting a real number of rotations of the motor means while the pump is driving, and second display means for displaying a real number of rotations detected by the real number of rotations detecting means, the operating unit operating the dial means based on the set number of rotations and the real number of rotations respectively displayed on the first and second display means, and adjusting the number of rotations of the motor means.

According to the medical pump driving device of the present invention, the present set number of rotations is displayed by the first display means when the pump is stopped. Since the operator may monitor the display, and operate the dial in accordance with the set number of rotations, the pump driving operation can be safely begun. Therefore, safety of operation can be improved, and the complication of operation can be overcome.

Moreover, the medical pump driving device of the present invention further comprises corrected value calculating means for calculating a corrected value to correct the set number of rotations based on the set number of rotations and the real number of rotations, corrected value storing means for storing the corrected value calculated by the corrected value calculating means, and number of rotations correcting means for correcting the set number of rotations by the corrected value stored in the corrected value storing means.

According to the above-structured medical pump driving device, the present set number of rotations is displayed by the first display means when the pump is stopped. On the other hand, during the pump driving, the real number of rotations of the motor is detected, and the detected real number of rotations of the motor is displayed by the second display means. The corrected value is calculated from the real number of rotations and the set number of rotations, and the set number of rotations is corrected by the corrected value. Therefore, even after the the pump driving is started, the first display section displays the correct set number of rotations at this time, and safety of operation can be improved.

Moreover, the medical pump driving means of the present invention further comprises display changing means for changing the display of the first display means and that of the second display.

Furthermore, the medical pump driving device of the present invention further comprises indicating means for indicating whether first display means is used or second display means is used. The display by the first display means and the display by the second display means may be performed on the same screen. A medical pump driving device comprises pump means for circulating liquid through liquid passages connected to a medical device; motor means for driving the pump means; a flow connector attached to the liquid passage and having substantially the same diameter as that of the liquid passage; a sensor unit having a flow velocity measuring sensor detachably attached to the flow connector to measure the flow velocity of liquid in the liquid passage; first memory means for storing data relating to the diameter of the liquid passage and data to correct a measuring error of the sensor unit; second memory means for temporarily storing, as data, the flow velocity of liquid detected by the flow velocity measuring sensor; electrical connectors for electrically connecting the flow velocity measuring sensor and the second memory means; calculating means for arithmetically calculating the flow rate of liquid from data read from the first and second memory means; and means for controlling the flow rate of liquid in the liquid passages responsive to the flow rate of liquid thus calculated.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is a schematic view showing a priming system using a pump driving device of a first embodiment of the present invention;

FIG. 2 is a front view showing an operation panel in the pump driving device of the first embodiment of the present invention;

FIG. 4 is a characteristic view showing one example of the relationship between a setting voltage and the number of rotations of the D.C. motor;

FIG. 6 is a block diagram showing a circuit of a control section of a medical pump driving device relating to a second embodiment of the present invention;

FIG. 13 is a partly sectional view showing the sensor unit viewed in a direction perpendicular to the liquid-circuit;

FIG. 14 is a partly sectional view showing the sensor unit viewed in a direction along the liquid-circulating circuit;

FIG. 15 is a diagram showing the sensor unit in a state of being released;

FIG. 16 is a partly sectional view showing the sensor unit being set in place.

DETAILED DESCRIPTION OF THE PREFERRED EMBODIMENTS

Figure 3:
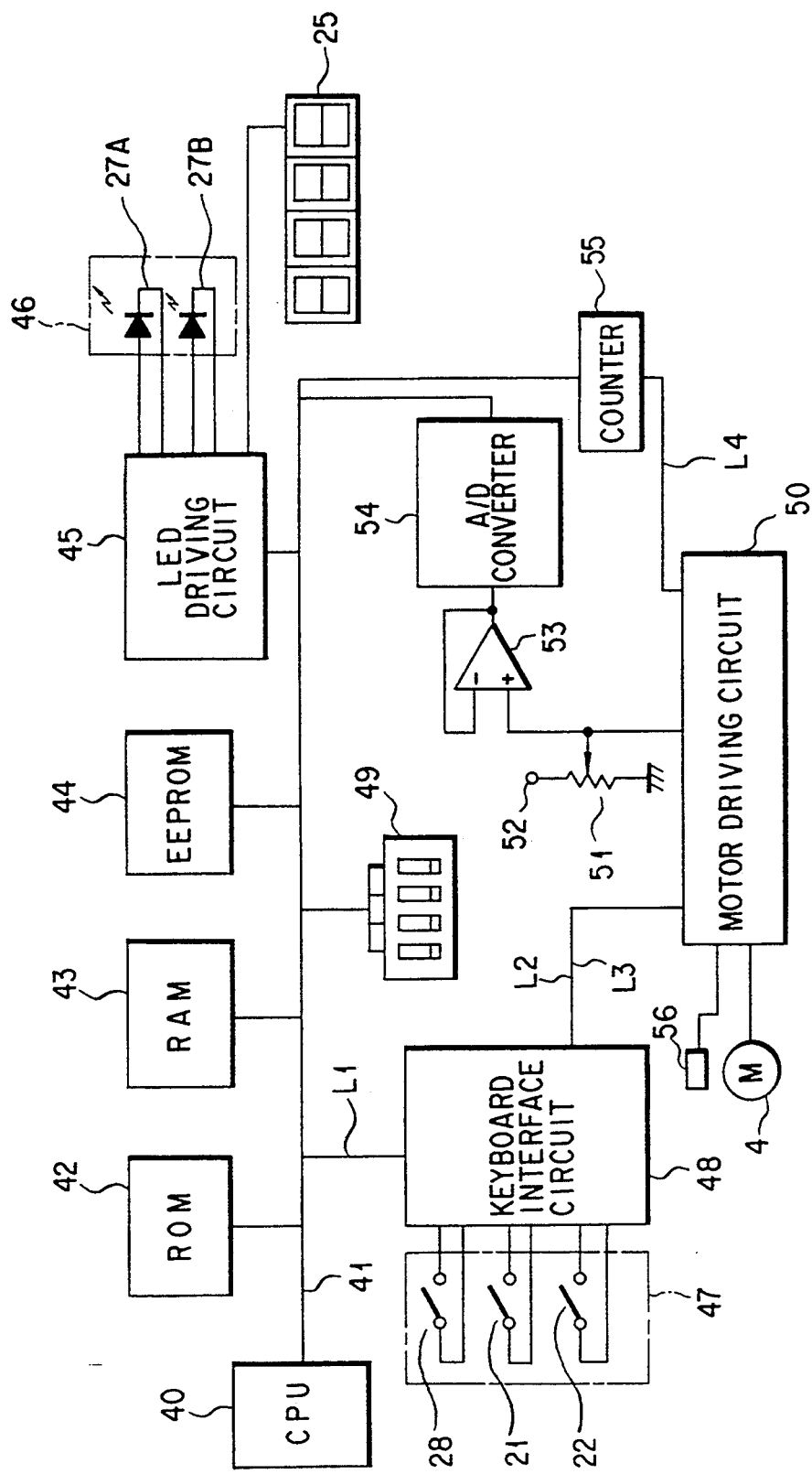
FIG. 3 is a block diagram showing a circuit of the medical pump driving device relating to the first embodiment of the present invention.

Embodiments of the present invention will be explained with reference to the drawings.

FIG. 1 is a schematic view showing a priming system using a pump driving device of a first embodiment of the present invention. In the priming system, there is provided an artificial lung 1 to be used as a medical device having a liquid channel.

In the housing of the artificial lung 1, a large number of bundles of porous hollow fiber membranes are contained. In the porous hollow fiber membranes, there are formed a large number of through pores, which are communicated the inner and outer portions of the membranes. A blood inflow port 11 is formed at the upper portion of the housing, and an blood outflow port 17 is formed at the lower portion of the housing. A blood chamber is formed between the blood inflow port 11 and the blood outflow port 17. The blood chamber is defined by the inner surface of the housing and the outer surface of the porous hollow fiber membranes, and functions as a blood channel.

At the time of using the actual external circulation, vein blood taken out of the human body flows into the blood chamber of the artificial lungs 1 from the blood inflow port 11, and the vein blood contacts the outer surface of the porous hollow fiber membranes. Then, oxygen containing gas flows in the porous hollow fiber membranes. Oxygen in gas passes through the holes of the porous hollow fiber membranes and penetrates into 10 blood. Then, oxygen-rich blood is passed through the blood outflow port 17 and returned to an artery of the human body from the artificial lung 1.

In this case, since the porous hollow fiber membranes have a property in which gas is passed but liquid is not passed, the artificial lung 1 itself also have the function as bubble removing means.

The blood inflow port 11 of the artificial lung 1 is communicated with a discharge port 13 of a centrifugal pump 2 through a tube 12. A centrifugal pump 2 is used as the medical pump. A rotator of the centrifugal pump 2 is driven to be rotated by a motor 4. The rotator of the pump 2 is connected to the motor 4 by magnetic connecting means and the like. The motor 4 is connected to an output section of a motor driving device so that the drive of the motor 4 is controlled.

A container 3, in which harmless liquid to the human body such as Ringer's solution is contained, is provided at the upper stream side of the centrifugal pump 2. The container 3 is communicated with the middle portion of a tube 16 through a branch pipe 15. One end of the tube 16 is communicated with an inflow port 14 of the centrifugal pump 2. The other end of the tube 16 is connected to the blood outflow port 17 of the artificial lungs 1.

A sensor 6 is provided in a tube 12 of the lower stream of the centrifugal pump 2 and connected to an input section of the motor driving device 5. The sensor 6 has a function of detecting whether or not bubbles are formed in the tube 12 of the lower stream, and has a function of measuring the flow rate of liquid passing through the tube 12. The sensor 6 is favorably used an ultrasonic sensor.

An operation of the priming system will be explained.

Ringer's solution passes through the branch pipe 15 and flows in the tube 16 from the container 3, and further flows in the centrifugal pump 2 from the inflow port 14. Then, Ringer's solution is rotated in the centrifugal pump 2, centrifugal force is applied to Ringer's solution. Thereby, Ringer's solution is forcefully sent to the blood inflow port 11 of the artificial lung 1 from the discharge port 13.

At this time, the bubbles adhered to the channel of the centrifugal pump 2 and the inner wall of the tube 12 are moved to the inflow port 11 together with Ringer's solution. The bubbles flow in the blood chamber of the artificial lungs 1 together with Ringer's solution. The bubbles passes through the large number of holes of the porous hollow fiber membranes, and then, are discharged outside from the artificial lungs 1. Ringer's solution flows into the tube 16 from the blood outflow port 17 of the artificial lungs 1, and is further returned to the centrifugal pump 2. In this way, the bubbles are removed while Ringer's solution is circulated in a circuit containing the centrifugal pump 2 and the artificial lungs 1.

An operation panel 20 of the pump driving device 5 will be explained with reference to FIG. 2.

The operation panel 20 is structured such that an operator can easily manually operate the panel. The operation panel 20 comprises a start key 21, a stop key 22, a message display 23, a dial 24, a display 25 displaying a number of rotations, and a liquid flow rate display 26. The start key 21 is used to instruct the motor 4 to start driving. The stop key 22 is used to instruct the motor 4 to stop driving. The message display 23 is a liquid crystal display (LCD) for communicating various messages to the operator. The dial 24 is used to adjust the number of rotations of the centrifugal pump 2. The display 25 is a display for indicating the setting number of rotations of the centrifugal pump 2 when the centrifugal pump 2 is stopped, and displaying the real number of rotations of the centrifugal pump 2 when the centrifugal pump 2 is driven. The liquid flow rate display 26 is a display for indicating liquid flow rate such as Ringer's solution.

On the upper portion of the display 25, there are provided a set display section 27A and a real display section 27B both which are formed of a light emitting diode (LED). The set display section 27A informs that value display by the display 25 is the setting number of rotations when the centrifugal pump 2 is stopped. The set display section 27A is turned on when the centrifugal pump 2 is stopped. The real display section 27B informs that value display by the display 25 is the real number of rotations when the centrifugal pump 2 is driven. The real display section 27B is turned on when the centrifugal pump 2 is driven.

A set key 28 is provided in the liquid flow rate display 26. The set key 28 is used to instruct a correcting operation to be explained later during the drive of the centrifugal pump 2.

A control circuit of the display 25 of the pump driving device 5 will be explained with reference to FIG. 3.

The pump driving device 5 comprises a central processing unit (CPU) 40. The CPU 40 is connected to each part of the device through a bus 41 such as a data bus. A ROM 42 is a memory containing a program for performing various control of the pump driving device 5, and a program in which a difference between the setting number of rotations of the motor 4 and the real number of rotations is detected and a correction circulation is performed. A RAM 43 is a memory for temporarily storing various data necessary to perform the control of the pump driving device 5.

An EEPROM (Electrical Erasable Programmable Read Only Memory) 44 is a partially writable memory for storing a corrected value based on the difference between the setting number of rotations and the real number of rotations of the motor 4. It is noted that a backup of the RAM 43 may be formed and that the corrected value may be stored in the backup.

A LED driving circuit 45 controls the display 25 shown in FIG. 2 and an informing section 46, which is formed of the set display section 27A and the real display section 27B, based on a control signal sent from the CPU 40.

Moreover, a keyboard interface circuit 48 is connected to the CPU 40. The keyboard interface circuit 48 sends various instruction signals to be outputted from a switching circuit 48, which is formed of keys 21, 22, and 28, to the CPU 40 or a motor driving circuit 50.

In this case, a set signal to be outputted from the set key 28 (hereinafter called as "set signal") is passed through a line L1 and sent to the CPU 40. Also, a start signal to be outputted from the start key 21 (hereinafter called as "start signal"), and a stop signal to be outputted from the stop key 22 (hereinafter called as "stop signal") are passed through a line L2 and sent to the motor driving circuit 50, respectively.

The CPU 40 performs the correction calculation of the set number of rotations of the centrifugal pump 2 based on the program, which receives the set signal and stored in the ROM 42, and stores the corrected value in the EEPROM 44, and carries out the display of the value display 25 based on the corrected set number number of rotations. It is noted that an inner set switch 49 is connected to the CPU 40 and that the CPU 40 does not perform the corrected calculation in the case that the inner set switch 49 is not pressed.

A motor driving circuit 50 starts the drive of the motor 4 on receipt of the start signal, and stops the drive of the motor 4 on receipt of the stop signal to be outputted from the stop key 22.

A variable resistor 51 is connected to the motor driving circuit 50. A reference voltage is applied to the variable resistor 51 from a voltage terminal 52, and a division voltage value of the reference voltage is applied to the motor 4 by the motor driving circuit 50. Then, if the dial 24 is rotated, the divisional voltage value of the reference voltage can be changed.

The motor 4 serving as a driving source of the centrifugal pump 2, D.C. motor, whose number of rotations can be easily controlled, is generally used. The number of rotations of the D.C. motor is proportional to the driving voltage. Due to this, if the variable reference voltage is current-amplified and applied to the motor, the number of rotations can be easily controlled.

FIG. 4 is a graph showing the relationship between the control voltage (V) of the number of rotations of the motor (horizontal axis) and the number of the rotations (RPM) (vertical axis) relating to the D.C. motor. As is obvious from the figure, the number of rotations of the D.C. motor is proportional to the control voltage (set voltage).

As shown in FIG. 3, the divisional voltage outputted from the variable resistor 51 is also applied to a positive input terminal of an operational amplifier 53. A negative input terminal of the operational amplifier 53 is connected to the output terminal. Moreover, the output terminal is connected to an input terminal of an A/D converter 54.

The operational amplifier 53 is used to prevent the divisional voltage to the motor driving circuit 50 from being changed. In other words, the operational amplifier 53 has a function in which the influence of the voltage variation of the A/D converter 54 is not exerted on the motor driving circuit 50.

The A/D converter 54 converts the divisional voltage (analog value) outputted from the operation amplifier 53 to a digital value, and outputted to the CPU 40. The CPU 40 calculates the set number of rotations of the centrifugal pump 2 based on the output signal from the A/D converter 54, and controls the display 25 to display the calculated set number of rotations. At this time, the CPU 40 turns on the set display section 27A and turns off the real display section 27B. The operator can confirm the set number of rotations by seeing the turn-on of the set display section 27A.

A sensor 56 for detecting the number of rotations is provided close to the motor 4. The sensor 56 detects the real number of rotations of the motor 4 at the time of the drive of the centrifugal pump 2. The sensor 56 has a function of supplying pulse signals to a counter 55 through the motor driving circuit 50 and a line L4 in accordance with the real number of rotations.

The counter 55 counts the number of pulse signals, and sends the counted pulse signals to the CPU 40. The CPU 40 calculates the real number of rotations of the motor 4 on receipt of the the counted pulse signals, and controls the display 25 to display the calculated real number of rotations. At this time, the CPU 40 turns off the set display section 27A and turns on the real display section 27B. The operator can confirm the real number of rotations by seeing the turn-on of the real display section 27B.

Figure 5A:
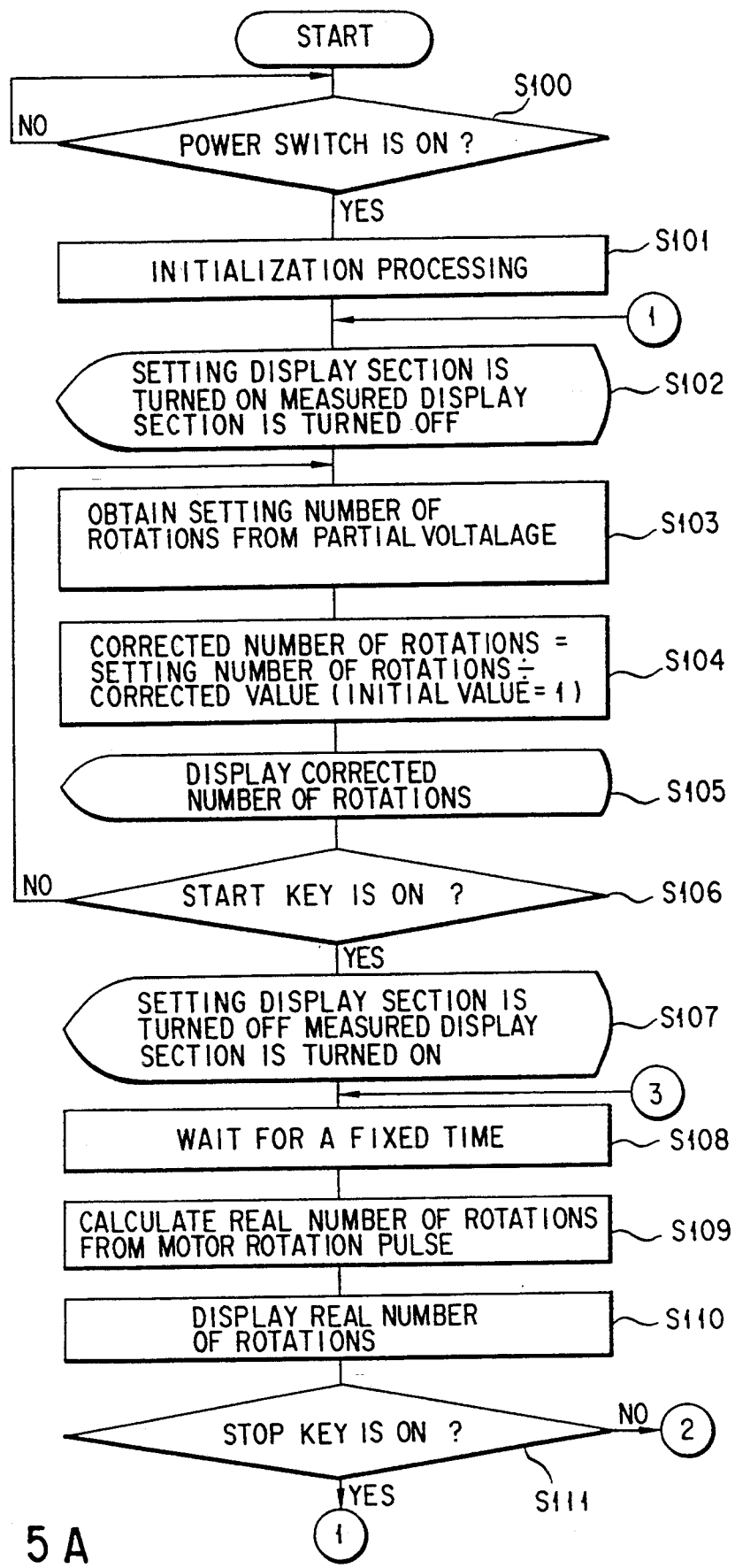
FIGS. 5A and 5B are flow charts explaining the number of rotations display operation of the pump driving device of the first embodiment, respectively.
Figure 5B:
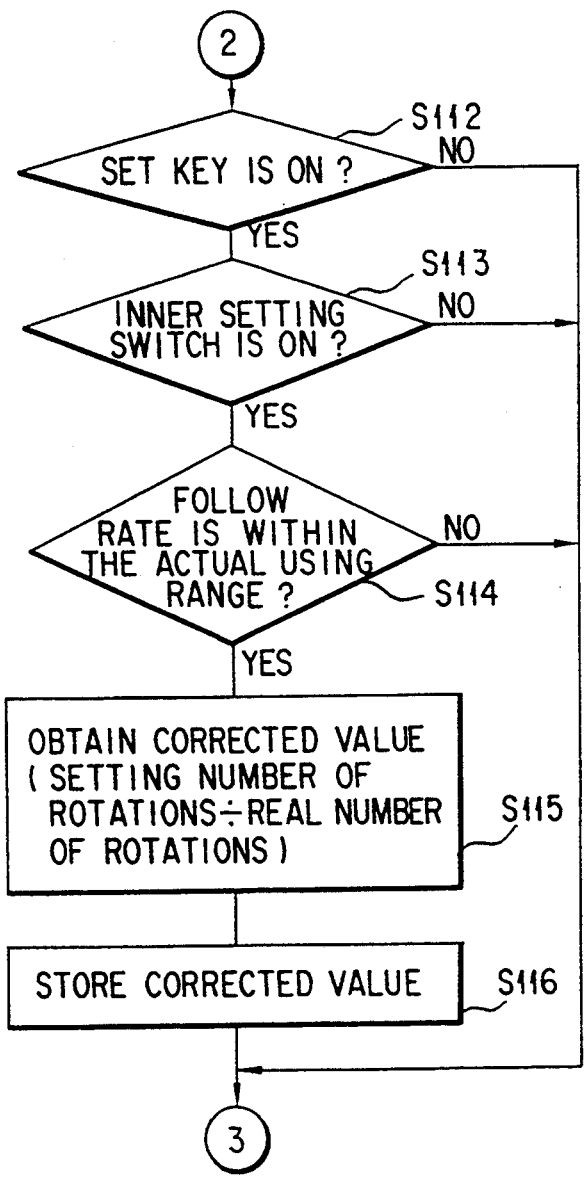

A display operation of the number of rotations of the medical pump device 5 of a first embodiment will be explained with reference to the flow charts of FIGS. 5A and 5B.

If a power switch (not shown) is turned on (step 100; YES), the CPU 40 performs an initializing (step 101). If the initializing is ended, the CPU 40 turns on LED of the set display section 27A, and maintains the turn-off state of LED of the real display section 27B (step 102).

The CPU 40 takes in the division voltage value outputted from the variable resistor 51 through the A/D converter 54, and calculates the set number of rotations (step 103). Then, the set number of rotations is divided by the corrected value, thereby obtaining a corrected number of rotations (step 104). In this case, since an initial value of the corrected value is "1", this corrected number of rotations is equal to the set number of rotations. Sequentially, the CPU 40 controls the display 25 to display the corrected number of rotations (step 105).

Thereafter, if the operator turns on the start key 21 (step 106; YES), the start signal is sent to the motor driving circuit 50 through a line L2. If the start signal enters the motor driving circuit 50, the motor 4 is rotated at the set number of rotations, and the centrifugal pump 2 is started up.

While the centrifugal pump 2 is driving, the set display section 27A is turned off, and the real display section 27B is turned on (step 107). After passing a fixed time (step 108), the CPU 40 calculates the real number of rotations based on the count pulse to be outputted from the counter 55 (step 109), and controls the display 25 to display the real number of rotations (step 110).

After a predetermined time is passed from the drive beginning of the centrifugal pump 2, the CPU 40 discriminates whether or not the stop key 22 is turned on (step 111). If the stop key 22 is turned on (YES), the CPU 40 returns to step 102. If the stop key 22 is turned off (NO), the CPU 40 goes to step 112 shown in FIG. 5B, and discriminates whether or not the set key 28 is turned on (step 112). If the set key 28 is turned on (YES), the CPU 40 discriminates whether or not the inner set switch 49 is turned on (step 113; YES or NO). If the inner set switch 49 is turned on (YES), the CPU 40 discriminates whether or not the flow rate of liquid (Ringer's solution) is within "a real using range of liquid flow rate" (step 114; YES or NO). It is noted that the discrimination of step 114 is performed based on a real liquid flow rate measured by the sensor 6. The significance of such discrimination lies in preventing excessive amount of liquid from flowing in the human body so as to ensure safety.

In this case, the "real using range of liquid flow rate" is is a range of the flow rate, which is determined by the amount of blood flowing in the human body in the normal condition.

If the flow rate is within the real using range (YES), the CPU 40 obtains the real number of rotations of the motor 4 from the latest pulse signal. Further, the CPU 40 obtains a corrected value from the real number of rotations and the set number of rotations (=the set number of rotations is divided by the real number of rotations) (step 115). Then, the set number of rotations is corrected by use of the corrected value.

It is preferable that the calculation of the corrected value is not performed in the case that the real number of rotations of the motor 4 deviates from the real using range too much. Moreover, if the calculated corrected value is extremely large, the number of rotations is not preferably corrected since it is considered that a trouble occurs in some portions.

Sequentially, the CPU 40 controls the corrected value to be stored in the EEPROM 44 (step 116), and goes back to step 108. If the set key 28 is not turned on (step 112; NO), the inner set switch 49 is not turned on (step 113; NO), or the flow rate is not in the real using range (step 114; NO), the CPU 40 determines that the correction is not needed, and goes back to step 108.

According to the pump driving device 5 of the first embodiment, before the centrifugal pump 2 is used, that is, when the centrifugal pump 2 is stopped, the set display section 27A is turned on, and the corrected set number of rotations is displayed on the display 25 based on the corrected value stored in the EEPROM 44.

Therefore, the operator may the dial 24 as watching the displayed set number of rotations. Due to this, it is possible to save the troublesome in which the scale of the dial 24 is once returned to the minimum value and the number of rotations is increased. As a result, the operator can start safely the pump driving operation, so that the operator is relieved from the complicated operation.

Moreover, according to the pump driving device 5 of the first embodiment, while the centrifugal pump 2 is driving, the difference between the set number of rotations and the real number of rotations is detected, the corrected value of the set number of rotations is obtained based on the difference, and the corrected value is stored in the EEPROM 44. Then, the set number of rotations is renewed by use of the corrected value. Therefore, after renewing the set number of rotations, the set number of rotations having high precision is displayed on the display 25, and reliability of the operation is improved.

Moreover, as long as the inner set switch 49 is provided and is not turned on, the correcting calculation is not performed. Due to this, the safe operation can be performed since there is no possibility that a third party will change the set number of rotation without the operator's permission.

The present invention has been explained by the above embodiment. However, the present invention is not limited to the above embodiment, and various modifications may be made in the range of the gist of the present invention.

For example, in the above first embodiment, in order to ensure safety, the start signal and the stop signal were directly supplied to the motor driving circuit 50 without sending the start signal and the stop signal to the CPU 40, respectively. However, in the case that operator is able to take no notice of safety, the set signal, the start signal, and the stop signal are once sent to the CPU 40, and these signals serving as control signals may be supplied to the motor driving circuit 50 from the CPU 40.

According to the above first embodiment, in the operation panel 20, the set display section 27A and the real display section 27B were provided on the display 25 and the set number of rotations of the motor 4 and the real number of rotations were informed the operator. However, for displaying the real number of rotations without providing the display sections 27A and 27B, the discrimination between the set display and real display may be performed by blinking the display 25.

Moreover, the discrimination between the set display and the real display may be performed by two-color-emitting the display 25. Thereby, the occupied space of the display 25 can be reduced.

A second embodiment will be explained. The explanation of the portions, which are common to the portions of the first embodiment, will be omitted.

A medical pump driving device of the second embodiment is incorporated in the priming system of FIG. 1.

As shown in FIG. 6, a motor 204 is controlled to be constantly or intermittently rotated by a motor driving circuit 250. By controlling the rotation of the motor 204, liquid is constantly or intermittently transferred by the centrifugal pump 2.

According to the priming system of the second embodiment, since the centrifugal pump 2 is intermittently driven by the motor 204, a predetermined amount of Ringer's liquid is intermittently sent to the tube 12 from the discharge port 13 at a predetermined at a predetermined time distance. Since Ringer's liquid is intermittently transferred, a bubble adhered to the inner wall of the liquid channel of the tube 12 and the like is efficiently separated from the inner wall of the channel by the strength and weakness of the flow of Ringer's liquid. Thereafter, in the artificial lug 1, the bubble is removed outside. In this case, the bubble moving in the tube 12 is detected by the sensor 6.

Figure 7:
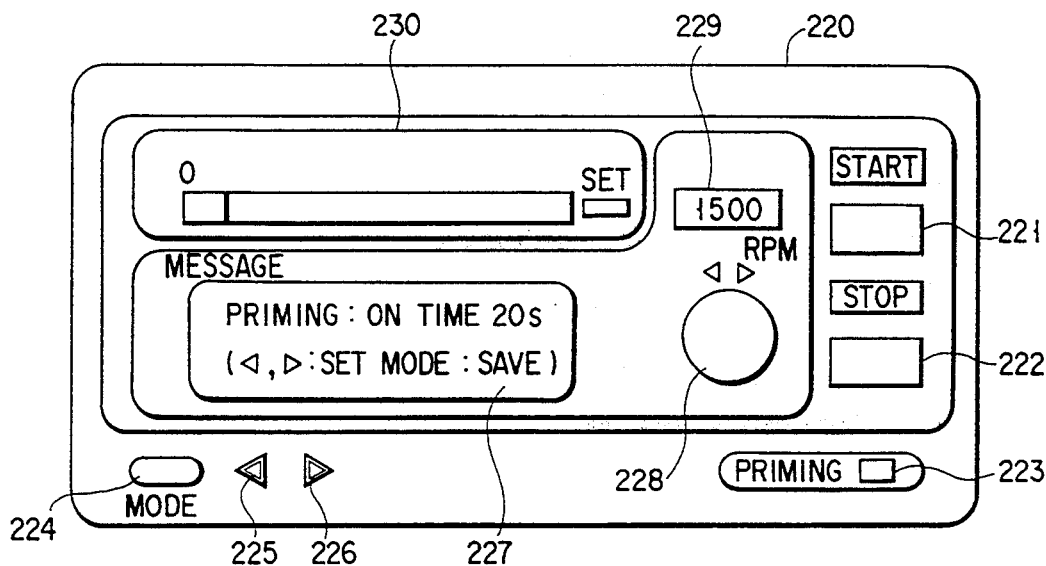
FIG. 7 is a front view showing an operation panel in the medical pump driving device of the second embodiment of the present invention.

As shown in FIG. 7, an operation panel 220 is provided in the pump driving device 5. In the operation panel 220, there are various type of keys such as a start key 221, a stop key 222, a priming key 223, a mode key 224, an up key 225, and a down key 226 are arranged. The start key 221 is a key by which an operator indicates the normal constant driving. The stop key 222 is a key by which the operator stops the drive of the motor 204. The priming key 223 is a key by which the operator indicates the intermittent drive of the motor 204. The mode key 224 is a key by which the operator changes various set values for the intermittent drive of the motor 204 to a predetermined set mode. The up key 225 is a key by which the operator increases the set value of the number of rotations of the motor 204. The down key 226 is a key by which the operator decreases the set value of the number of rotations of the motor 204.

If the priming key 223 is depressed two times, a release signal of a priming signal is outputted similar to the case of the stop key 222. Moreover, every time the mode key 224 is depressed, the set mode is different, so that the set value having different voltage and driving time can be changed.

Moreover, the operation panel 220 comprises a message display 227, a dial 228, a number of rotations display 229, and a liquid flow rate display 230. The message display 227 is formed of a liquid crystal display (LCD) for giving various messages to the operator. The dial 228 is used to control the number of rotations of the centrifugal pump 2. The number of rotations display 229 is used to display the number of rotations of the motor 204. The liquid flow rate display 230 is used to display the liquid flow rate of Ringer's liquid and the like.

FIG. 6 is a block diagram showing the main parts of the circuit structure of the pump driving device 5. The pump driving device 5 comprises a CPU 240. The CPU 240 is connected to each part of the device through a bus 241 such as data bus. A ROM 242 is a memory in which a program for performing various types of control of the pump driving device 5. A RAM 243 is a memory for temporarily storing various data necessary to perform the control of the pump driving device 5.

An EEPROM 244 is a nonvolatile memory, which is partially selectively changeable, and which is used to store various types of set values such as a priming high voltage (e.g., 8 V) for intermittently driving the centrifugal pump 2, a priming low voltage (e.g., 1 V), driving time (e.g., 2 seconds) at the priming high voltage, driving time (e.g., 1 second) at the priming low voltage, and one cycle (e.g., 3 seconds) of the intermittent driving.

Moreover, the message display 227 is connected to the CPU 240. The message display 227 interactively displays various types of messages during the drive of the motor.

Furthermore, a keyboard interface circuit 245 is connected to the CPU 240. The keyboard interface circuit 245 sends signals, which except the start signal and the stop signal from the various types of signals outputted from a switch circuit 246 comprising keys 221 to 226, to the CPU 240. In this case, the "start signal" is a signal, which is outputted from a line L6 through the start key 221, and the "stop signal" is a signal, which is outputted from a line L7 through the stop key 222.

The CPU 240 outputs a priming signal on receipt of the signal outputted from the priming key 223. The CPU 240 receives the signal outputted from the mode key 224, and sets the mode to a set value change mode in which the set value of the intermittent drive stored in the EEPROM 244 is changeable. In the set value change mode, every time the up key 225 or the down key 226 is turned on, the set value is changed.

The priming signal is passed through the line L5, and supplied to one input terminal of an OR circuit 249 and one input terminal of a multiplexer 247, respectively. The start signal, which is outputted from the keyboard interface circuit 245, or the stop signal is supplied to the other input terminal of the OR circuit 249 and the other input terminal of the multiplexer 247, respectively.

The OR circuit 249 supplies the priming signal or the start signal (or stop signal) to the motor driving circuit 250. The motor driving circuit 250 controls the drive of the motor 204 on receipt of these signals. In other words, in the case that the priming signal enters the circuit 250, the motor 204 is intermittently driven. On the other hand, in the case that the start signal enters the circuit 250, the motor 204 is driven at a constant speed. Also, in the case that the stop signal enters the circuit 250, the drive of the motor 204 is stopped.

The multiplexer 247 has a function of selecting either the inputted priming signal or the start signal (or stop signal) and outputting a switch signal to an analog switch 248 through a line L8 based on the selected signal.

The analog switch 248 changes a movable contact 248c to a fixed contact 248a or a fixed contact 248b in accordance with the content of the switch signal. In other words, in the case that the priming signal is selected by the multiplexer 247, the movable contact 248c is changed to the fixed contact 248a as shown in the broken line of the figure. On the other hand, in the case that the start signal (stop signal) is selected by the multiplexer 247, the movable contact 248c is changed to the fixed contact 248b as shown in the solid line of the figure. The movable contact 248c of the analog switch 248 is connected to the motor driving circuit 250.

The fixed contact 248b of the analog switch 248 is connected to a slider 253a of a variable resistor 253 for adjusting the number of rotations. The variable resistor 253 is connected to the motor driving circuit 250. In the case that the movable contact 248c is changed to the fixed contact 248b, the motor driving circuit 250 drives the motor 14 at the constant speed based on a voltage value set by the variable resistor 253, that is, the number of rotations. In this case, the voltage value is adjusted by that the operator rotates the dial 228.

Another fixed contact 248a of the analog switch 248 is connected to the CPU 240 through an D/A (digital/analog) converter 251. If the priming key 223 is turned on, the CPU 240 outputs the priming signal and outputs a set value for intermittent drive of the voltage value stored in advance from the EEPROM 244. The set value data signal is outputted to the D/A converter 251 through a line L9. The D/A converter 251 converts the set value data signal (digital signal) outputted from the CPU 240 to an analog signal, and supplies the analog signal to the fixed contact 248a of the analog switch 248.

The set value data signal supplied to the fixed contact 248a is supplied to the motor driving circuit 250 through the movable contact 248c. The motor driving circuit 250 has a function of intermittently driving the motor 204 based on the set value data signal.

Figure 8:
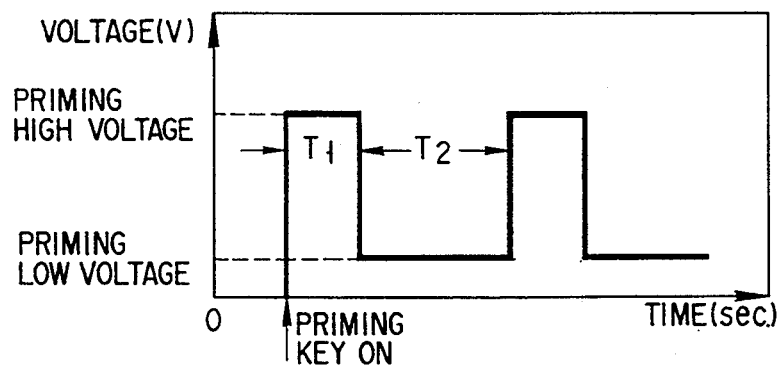
FIG. 8 is a characteristic view showing a motor driving voltage waveform to be used in the pump driving device of the second embodiment.

FIG. 8 shows a waveform characteristic showing one example of a pulse waveform of a motor driving voltage in a state that a horizontal axis shows time (second) and a vertical axis is a motor driving voltage. If the priming key 223 is turned on, the priming high voltage is supplied for time T1, thereafter priming low voltage is supplied for time T2.

Going Back to the FIG. 6, and the explanation will be continued. In the motor 204, there is provided a motor rotation detecting sensor (not shown) formed of, for example. Hole element. A rotation detecting pulse signal is supplied to a counter 252 from the sensor through the motor driving circuit 250. The counter 252 counts the number of supplied pulses, and the counted number of pulses is supplied to the CPU 240. The CPU 240 calculates the number of rotations of the motor 204 based on the number of pulses, and display the number of rotations on the display 229.

The bubble detecting sensor 6 is connected to the CPU 240 through a bubble detecting circuit 255. The bubble detecting circuit 255 sends a bubble detection signal to be outputted from the sensor 6 to the CPU 240. In the case that the bubble detection signal is not inputted within a fixed time by a timer built in the CPU 240, the CPU 240 discriminates that the priming operation is unnecessary, and stops the output of the priming signal.

An operation of a pump control operation of the medical pump of the second embodiment will be explained in detail with reference to FIGS. 9A to 9E.

If the power of the CPU 240 is turned on (step 300; YES), an initialization processing for each part is performed (step 301), thereafter the message display 220 displays a ready display (302).

The CPU 240 discriminates whether or not either the start key 221 or the priming key 223 is turned on. If the start key 221 is turned on (step 303; YES), the keyboard interface circuit 245 outputs a start signal to the motor driving circuit 250 through the OR circuit 249, and outputs a switch signal to the analog switch 248 through the multiplexer 247. The movable contact 248c of the analog switch 248 is connected to the fixed contact 248b. Thereby, the motor driving circuit 248 starts the constant drive of the motor 204 by the number of rotations based on the voltage value predetermined in advance by the variable resistor 253 (step 304).

Thereafter, in the case that the stop key 222 is turned on by the operator (step 305; YES), the drive of the motor 204 is stopped (step 306), and the operation is returned to the step 302.

On the other hand, in the case that the start key 221 is not turned on and the priming key 223 is turned on (step 303; NO), the CPU 240 discriminates that the priming signal is on (step 308), and outputs the priming signal to the motor driving circuit 250 through the OR circuit 249, and outputs the multiplexer 247. The multiplexer 247 outputs a switch signal to the analog switch 248 on receipt of the signal, and changes the movable contact 248c of the analog switch 248 to the fixed contact 248a. Thereby, the motor driving circuit 250 intermittently drives the motor 204 based on the predetermined set value.

In other words, the priming high voltage shown in FIG. 8 is outputted (step 309). After passing set time T1 (step 310; YES), the priming low voltage is outputted (step 311). Then, if the set time T2 is passed (step 312; YES), the operation goes back to the step 308. If the start key turned on (step 313; YES) before set time T2 is not passed (step 312; NO), the CPU 240 first performs the normal operation, and turns off the priming signal (step 314). Thereafter, the operation goes back to step 304, and the above-mentioned normal drive is executed.

Figure 9A:
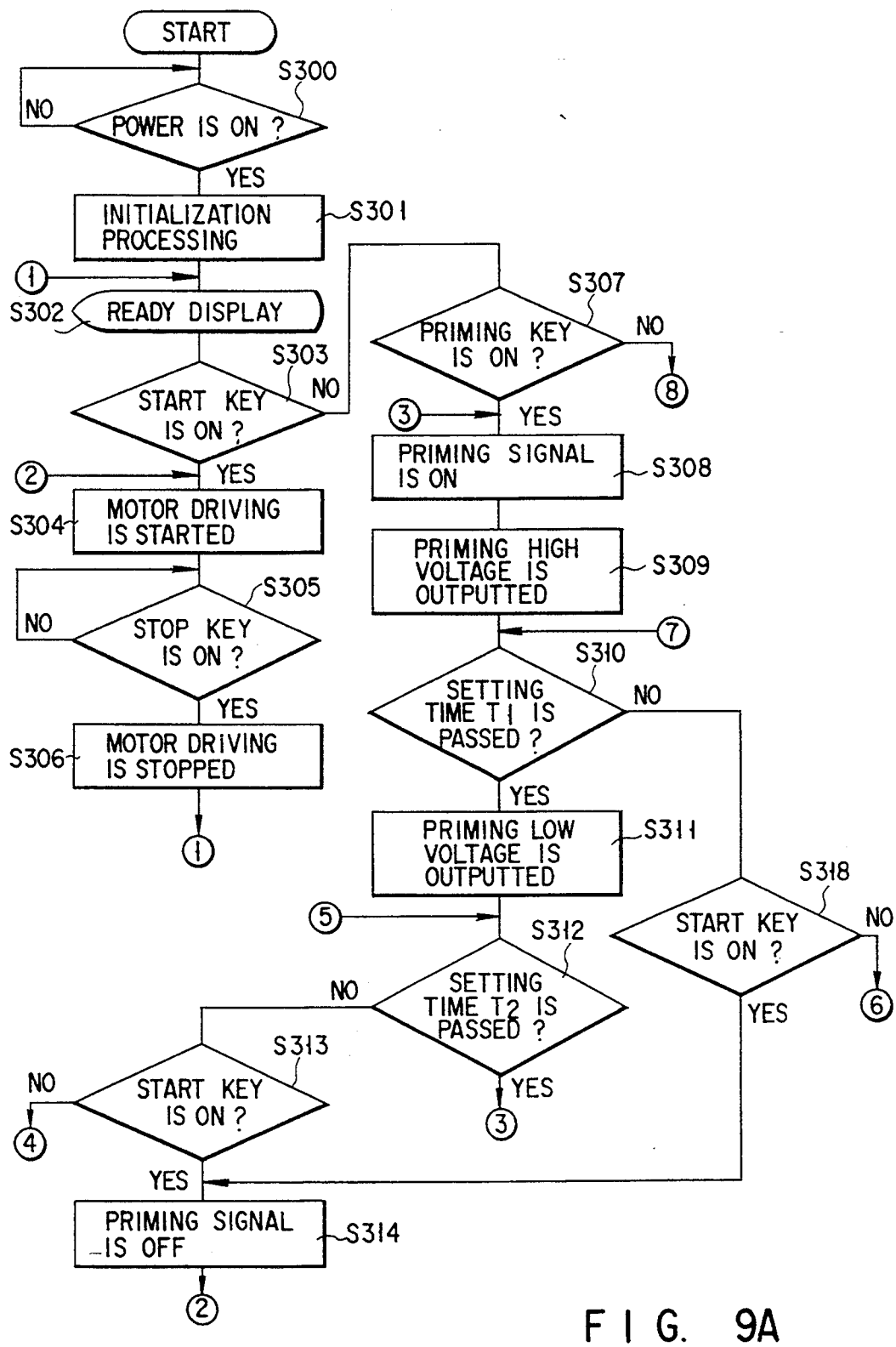
FIGS. 9A to 9E are flow charts explaining the number of rotations display operation of the pump driving device of the second embodiment, respectively.
Figure 9B:
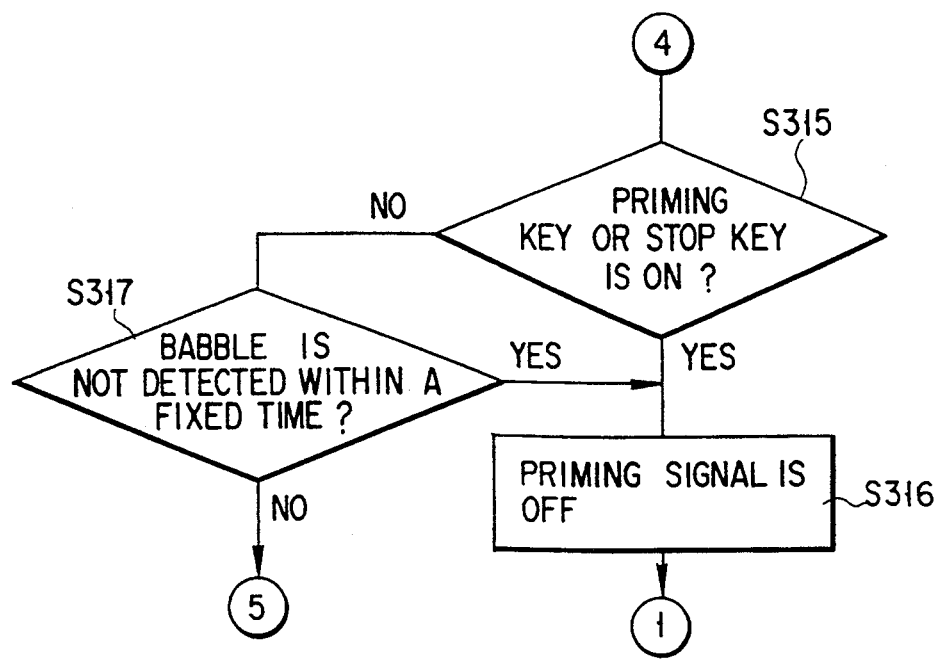

AS shown in FIGS. 9A and 9B, if the start key is not turned on (NO) in the step 313, the CPU 240 discriminates whether the priming key 223 is turned on again or the stop key 222 is turned on (step 315). If either the priming key 223 or the stop key 222 is turned on (YES), the priming signal is turned off (step 316), and the intermittent drive is stopped, and the operation goes back to the step 302.

On the other hand, if both keys are turned off (step 315; NO), the CPU 240 discriminates whether or not the bubble detection signal sent from the sensor 6 is detected within a fixed time (step 317). In the case that the bubble detection signal is not detected after passing the fixed time (YES), the priming signal is turned off (step 316), the operation goes back to step 302. Also, in the case that the bubble detection signal is detected after passing the fixed time (NO), the operation goes back to step 312.

If the operation goes back to the step 310 of FIG. 9A again, and the start key 221 is turned on before set time T1 is passed (step 318; YES), the CPU 240 turns off the priming signal (step 314), and the intermittent drive is stopped. The operation goes back to the step 304, and the normal operation is started.

Figure 9C:
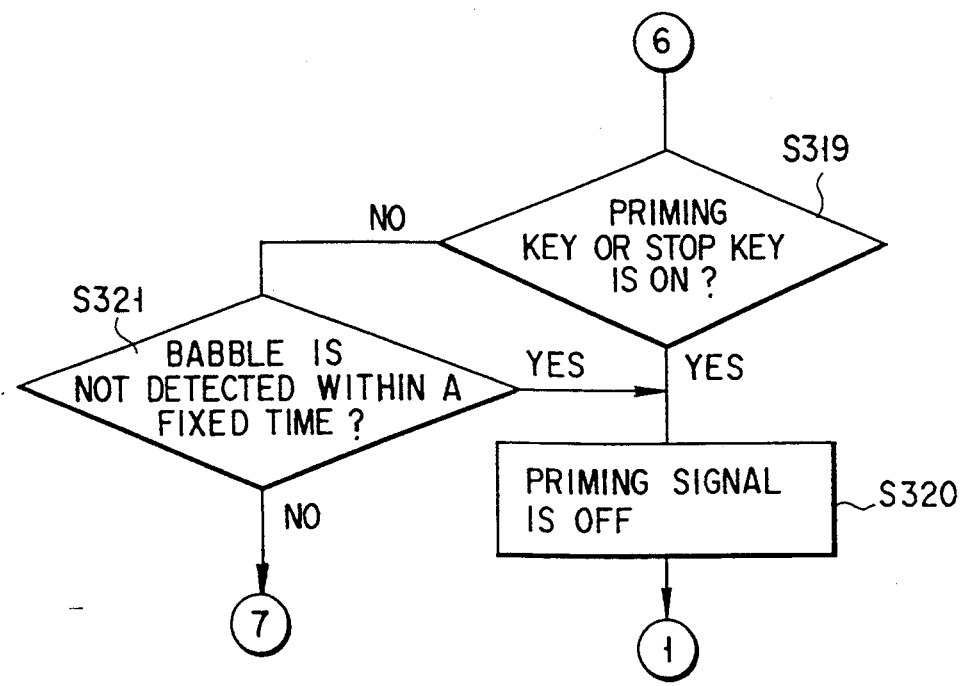

As shown in FIG. 9C, in the step 310, when the priming key 223 is turned on again or the stop key 222 is turned on (step 319; YES) without turning on the start key 221 (step 318; NO), the CPU 240 turns off the priming signal (step 320), and stops the driving, and the operation goes back to the step 302.

Moreover, if both keys are turned off (step 319; NO), the CPU 240 discriminates whether or not the bubble detection signal is detected from the sensor 6 for a fixed time (step 321). If the bubble detection signal is not detected after passing the fixed time (YES), the priming signal is turned off (step 320), thereafter the 10 operation goes back to the step 302. Also, if the bubble detection signal is detected after passing the fixed time (NO), the operation goes back to the step 310.

Figure 9D:
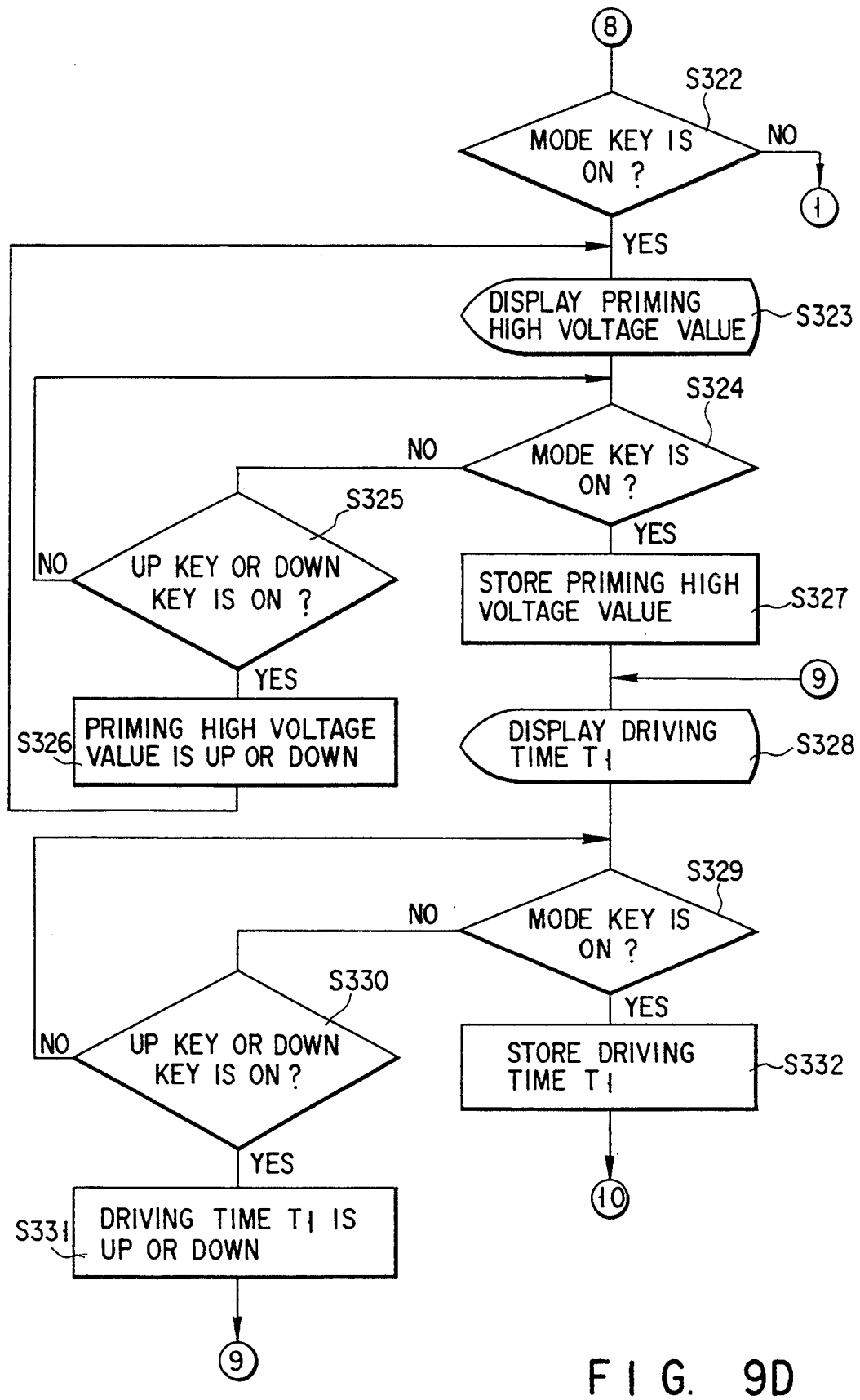
Figure 9E:
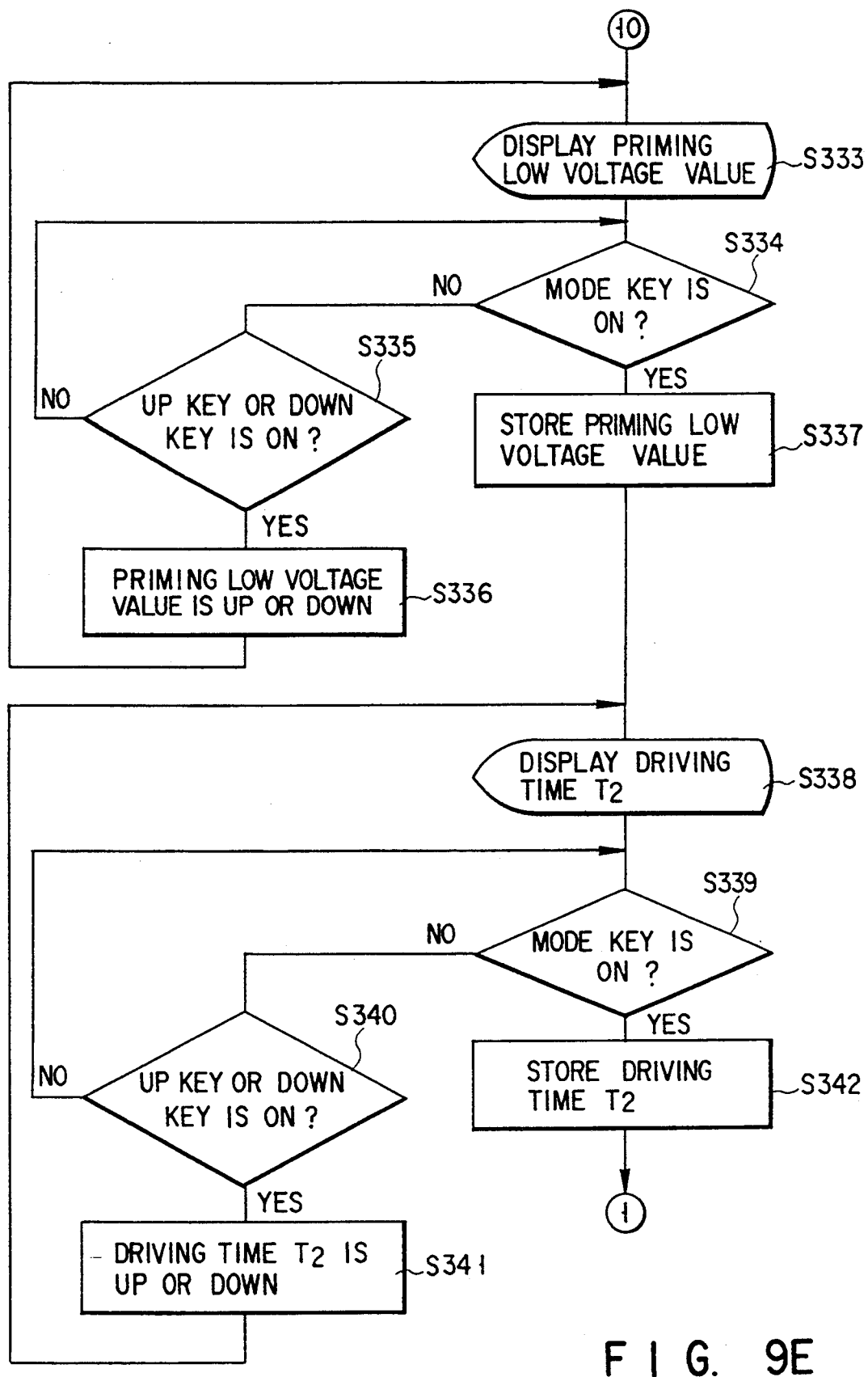
Figure 10:
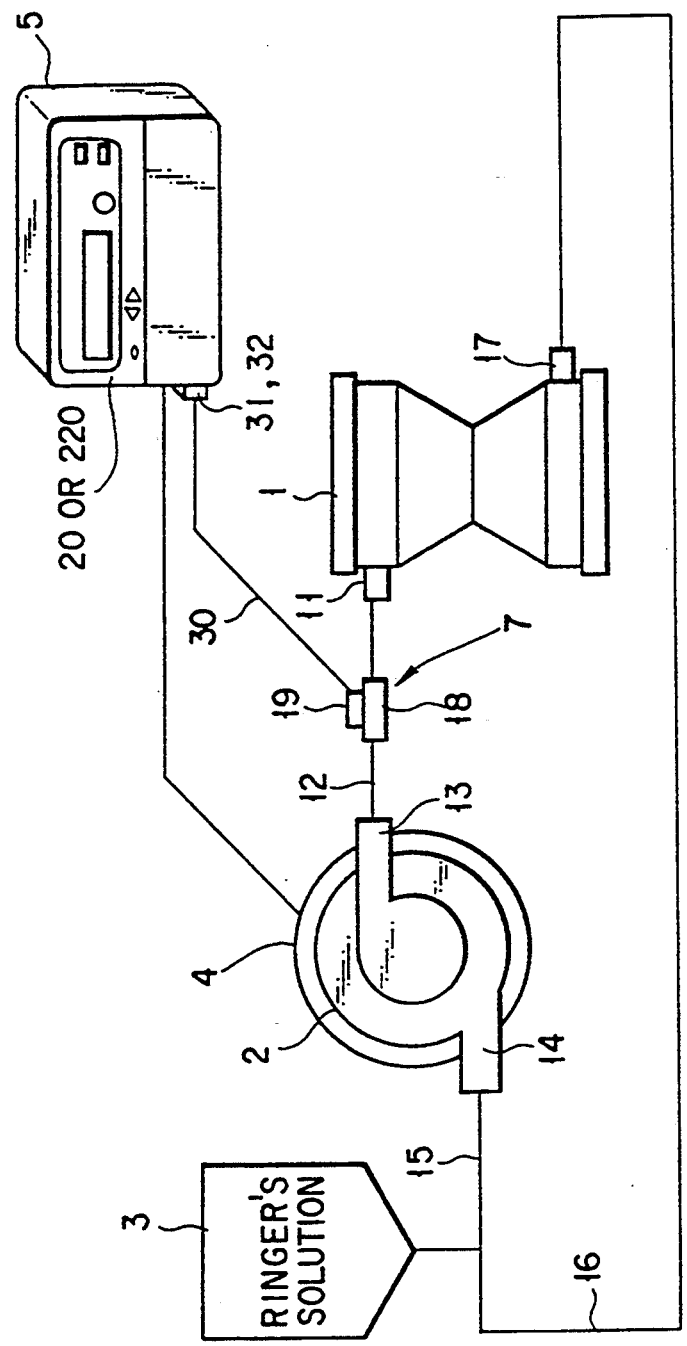
FIG. 10 is a block diagram schematically showing a blood-circulating circuit in which the medical pump driving device according to a third embodiment of the present invention is used.

An operation of the case in which the mode key 224 is turned on, and an operator changes various types of set values for intermittent drive will be explained with reference to FIGS. 9D and 9E.

In a state that neither start key 221 nor priming key 223 is turned on (step 307; NO), if the mode key 224 is turned on (step 322; YES), the priming high voltage is displayed on the message display 227 by the CPU 240 (step 223).

Thereafter, the CPU 240 discriminates whether or not the mode key 224 is turned on again (step 324). Then, if the mode key 224 is not turned on (NO), the CPU 240 discriminates whether or not the up key 225 or the down key 226 is turned on (step 325).

In the case that the up key 225 is turned on, the priming high voltage value is increased in accordance with the number of the turn-on of the up key 225. On the other hand, in the case that the down key 226 is turned on, the priming high voltage value is decreased in accordance with the number of the turn-on of the down key 226 (step 326). Thereafter, thee operation goes back to step 323, and the changed priming high voltage is displayed on the message display 227.

In step 324, if the mode key 224 is turned on again (YES), the CPU 240 stores the first priming high voltage value or the changed priming high voltage value in EEPROM 244 (step 327). Sequentially, the CPU 240 displays the driving time T1 of the priming high voltage on the message display 227 (step 328), and the operator again discriminates whether or not the mode key 224 is turned on (step 329).

If the mode key 224 is not turned on (NO), the CPU 240 discriminates whether or not the up key 225 or the down key 226 is turned on (step 330). In the case that the up key 225 is turned on, the driving time T1 is increased in accordance with the number of the turn-on of the up key. On the other hand, in the case that the down key 226 is turned on, the driving time T1 is decreased in accordance with the number of the turn-on of the down key (step 331). Thereafter, thee operation goes back to step 328, and the changed driving time T1 is displayed on the message display 227.

In the step 329, if the mode key 224 is turned on again (YES), the CPU 240 stores the first driving time T1 or the changed driving time T1 in EEPROM 244 (step 332). Sequentially, the CPU 240 displays the priming low voltage value on the message display 227 (step 333), and the operator again discriminates whether or not the mode key 224 is turned on (step 334).

If the mode key 224 is not turned on (NO), the CPU 240 discriminates whether or not the up key 225 or the down key 226 is turned on (step 335). In the case that the up key 225 is turned on, the priming low voltage value is increased in accordance with the number of the turn-on of the up key. On the other hand, in the case that the down key 226 is turned on, the priming low voltage value is decreased in accordance with the number of the turn-on of the down key (step 336). Thereafter, thee operation goes back to the step 333, and the changed priming low voltage value is displayed on the message display 227.

In the step 334, if the mode key 224 is turned on again (YES), the CPU 240 stores the first priming low voltage value or the changed priming low voltage value in EEPROM 244 (step 337). Therefore, the CPU 240 displays the driving time T2 of the priming low voltage on the message display 227 (step 338).

Sequentially, the CPU 240 discriminates whether or not the mode key 224 is not turned on (NO) again (step 339). If the mode key 224 is not turned on (NO), it is discriminated whether or not the up key 225 or the down key 226 is turned on (step 340). In the case that the up key 225 is turned on, the driving time T2 is increased in accordance with the number of the turn-on of the up key. On the other hand, in the case that the down key 226 is turned on; the driving time T2 is decreased in accordance with the number of the turn-on of the down key (step 341). Thereafter, the operation goes back to step 338, and the changed driving time T2 is displayed on the message display 227.

In the step 339, if the mode key 224 is turned on again (YES), the CPU 240 stores the first driving time T2 value or the changed driving time T2 in EEPROM 244 (step 342). Therefore, the CPU 240 goes back to the operation of step 302.

According to the pump driving device 5 of the second embodiment, the centrifugal pump 2 can be intermittently driven, so that the bubbles in the tube 12 and the artificial lungs 1 can be efficiently removed. Moreover, since the bubble removing operation is automatically performed, the operator's the manual operation is not needed during the operation. Therefore, the operator can perform the other work during the operation, and easily deal with a case of emergency.

Moreover, the set value of the voltage and the like for the intermittent drive can be displayed on the message display 227, and the set value can be changed in the form of interaction with the message display 227. Due to this, the operator's operation is extremely made easy.

The present invention has been explained by the above embodiment. However, the present invention is not limited to the above embodiment, and various modifications may be made in the range of the gist of the present invention.

For example, in the above second embodiment, the set value was changed by the up key 225 or the down key 226. However, the change of the set value may be made by a ten key.

Moreover, in the above embodiment, the changed set value was stored in EEPROM 244. In place of EEPROM 244, a backup of the RAM 243 may be formed and that the changed value may be stored therein.

Furthermore, in the above embodiment, the set value can be easily changed by depressing the up key 225 in the case that the set value change mode is set by the mode key 224. However, in order to prevent the set value from being easily changed by a person not concerned, the mode key may be provided in the inside of the device. Or, there may be provided the structure in which the set value change mode can not be set unless the power of the device is turned on as depressing a specific key.

In the above embodiment, in order to ensure safety, the start signal outputted from the start key 221 and the stop signal outputted from the stop key 222 were directly supplied to the motor driving circuit 250 without sending these signals to the CPU 240. However, in the case that there is little trouble in safety, similar to the other signals, these signals may be sent to the CPU 240, and outputted as control signals from the CPU 240 to the motor driving circuit 250.

The medical pump driving device according to a third embodiment of the present invention will be described referring to FIGS. 10–14. The medical pump driving device is applied to an external circulation system in this case. Description will be omitted for the same components as those of the first and second embodiments.

Figure 11:
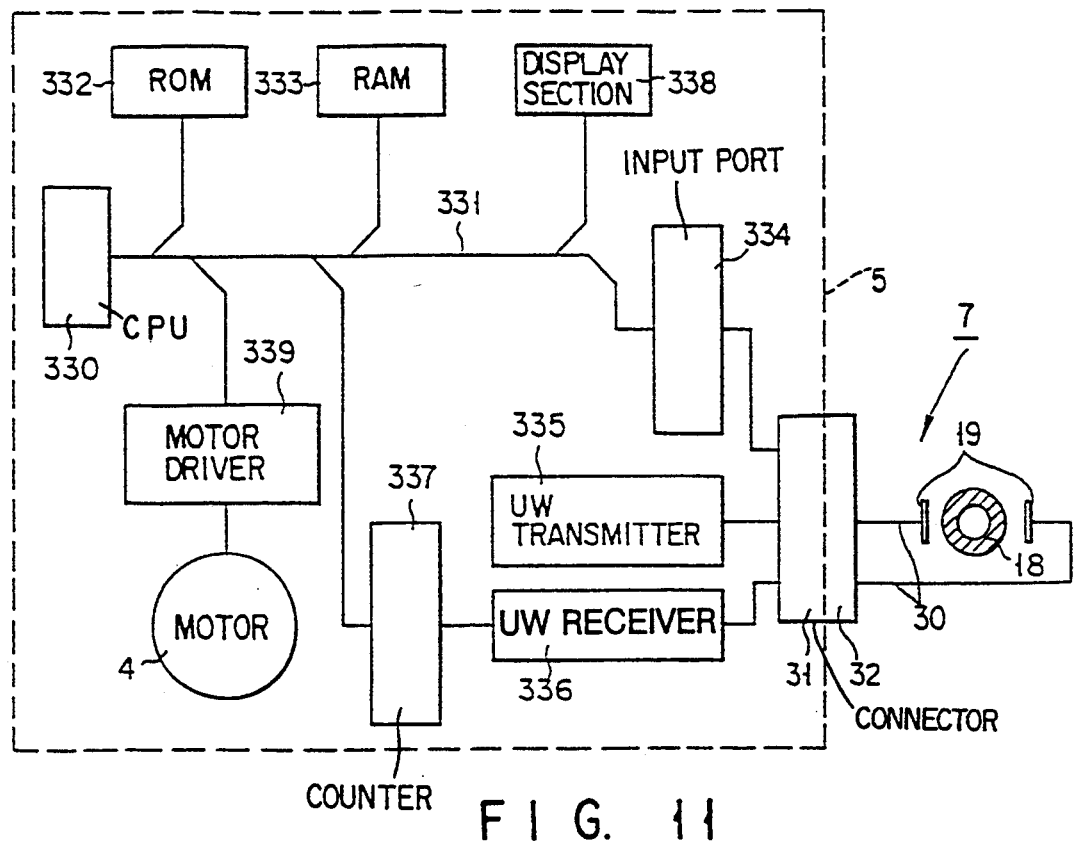
FIG. 11 is a circuit diagram showing a control circuit for the medical pump driving device according to the third embodiment of the present invention.

The flow connector 18 is attached to the tube 12 downstream of the centrifugal pump 2, and the sensor unit 7 is detachably attached to the flow connector 18. The sensor unit 7 includes a Doppler-type ultrasonic flowmeter having a pair of piezoelectric transducers 19. As shown in FIG. 11, one transducer 19 is connected to a transmitter 335 via connectors 31 and 32 and the other transducer 19 is connected to a receiver 336 via connectors 31 and 32.

As shown in FIG. 13, both ends of the flow connector 18 are fitted into the tubes 12. An inner diameter (diameter of a passage 18a) of the flow connector 18 is substantially the same as that of a passage 12a of the tube 12, and these passages 12a and 18a form a part of the liquid-circulating passage or circuit. That portion of the flow connector 18 which is fitted into the tube 12 is shaped conically and is also so shaped as not to easily come off of the tube 12. The flow connector 18 is made of hard synthetic resin such as polycarbonate or the like.

As shown in FIGS. 14, 14A–14C, 15, 16 and 16A, the sensor unit 7 can be attached to the flow connector 18 and can be detached therefrom by a single-step operation. In other words, the sensor unit 7 can be attached to the flow connector 18 when pushed down onto the connector 18, and can be removed from the connector 18 when the body member 8 is pulled up after the release levers 9 are pressed inwardly into the openings 8a in the body member 8 to release the resilient stoppers 75 from engagement with the periphery of a respective opening 8a (see FIG. 14). The pulled up position of body member 8 is shown in FIG. 15.

Holders 74 project downwardly from the clamp guide case 10 when the sensor unit 7 is released. When the sensor unit 7 is set in place, the portions of the slider 71 (FIGS. 15 and 16) and holders 74 are pushed into the clamp guide case 10 to clamp the sensor unit in place, as shown in FIG. 16.

Figure 14A:
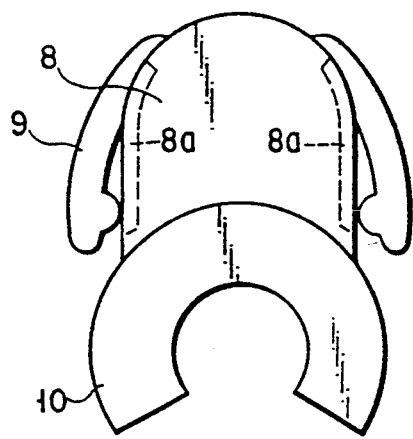
FIGS. 14A–14C are respective views of the elements of FIG. 14, shown enlarged and separated from each other.
Figure 14B:
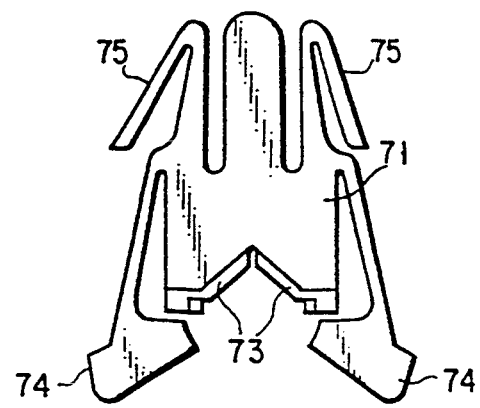
Figure 14C:
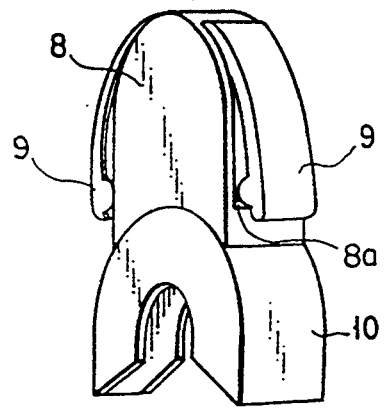
Figure 16A:
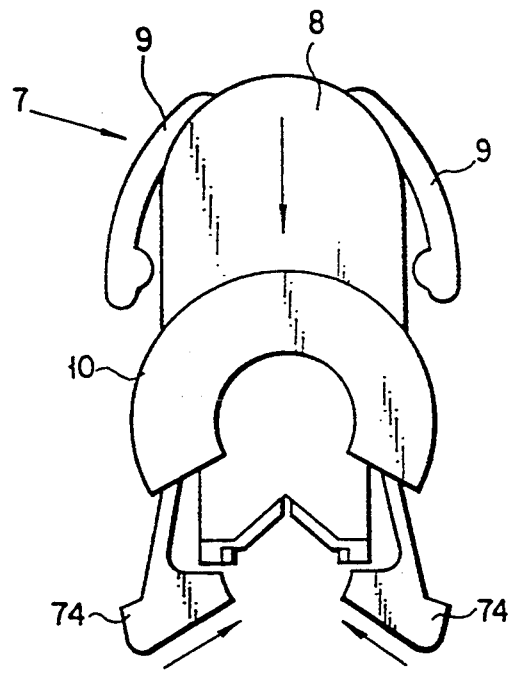
FIG. 16A shows the sensor unit of FIG. 16, with the tube 18 removed, and with arrows showing directions of movement of parts thereof.

FIGS. 14A–14C and 16A show additional views of the components of the clamping system. As shown in FIG. 14A, the body member 8, the release levers 9 and the guide case 10 are resin-like elastic members, and are formed as one integral piece. As shown in FIG. 14B, the slider 71 and the holders 74 are also resin-like elastic members, and are formed as one integral piece. As shown in FIGS. 14A and 14C, an opening 8a is formed in both opposite sides of the body member 8. As shown in FIG. 14, the stoppers 75 are releasably hooked on the periphery of each of the openings 8a. As shown in FIG. 16A, when the sensor unit 7 is pushed down, the holders 74 are deformed (pressed toward each other by the internal walls of the clamp guide case 10) so as to be close to each other to clamp tube 18 as shown in FIG. 16. As mentioned above, and as shown in FIGS. 14 and 16, when the levers 9 are pressed, the stoppers 75 are resiliently moved inwardly, and are detached from the periphery of each of the openings 8a. As shown in FIG. 15, when the clamp guide case 10 is thereafter pulled up, the holders 74 are elastically deformed to be separated from each other, and the flow connector 18 is detached from the holders 74.

As shown in FIG. 16, the upper central portion of the flow connector 18 has two flat surfaces 18a inclining and meeting each other, thus forming a ridge. The transducers 19 are located opposing the inclined flat surfaces 18a, respectively. Two expansion or projecting portions 18b extend from the sides of the flow connector 18. The tips of the holders 74 can abut (FIG. 16) on these expansion portions 18b, respectively, as described above, and can be released therefrom when the release levers 9 are pushed inwardly toward each other.

As shown in FIGS. 15 and 16, the transducers 19 are adhered to the lower portions 73 of the slider 71, inclined relative to each other, and opposing each other. While shooting or emitting ultrasonic waves from one transducer 19 to the liquid (or blood) flowing through the tube 12, the flow velocity of the liquid (or blood) is measured by the continuous-wave Doppler method which uses the Doppler effect.

The principle on which the flow velocity of blood is measured by the Doppler ultrasonic flowmeter will be described below.

When an ultrasonic wave having a frequency fo is emitted from one of the transducers 19 to the blood, it is reflected by components in the blood (or mainly by the group of blood cells). The ultrasonic wave thus reflected changes to have a frequency fs due to the Doppler shift and it is received by the other of the transducers 19. The flow velocity V of the blood can be calculated form the following equation (1) in which the Doppler frequency fd is included.

$$V = (C_2/2 \cos \theta) \times (fd/f0) \quad (1)$$

wherein fd=fs−f0 and $\theta = (\theta_1 - \theta_2)$. $\theta_1$ represents a complementary angle of an incident angle of the emitted ultrasonic wave, $\theta_2$ represents a complementary angle of an outgoing angle of the reflected ultrasonic wave reflected, and $C_2$ represents the sonic velocity in the blood (1580 m/sec). Preferably, the incident angle $\theta_1$ is 45° ±1°.

When the value of the flow velocity V calculated from equation (1) is multiplied by the cross-section area $\pi D^2/4$ of the blood-circulating passage 12a, 18a, the flow rate of blood circulated through the passage 18a can be obtained (the flow velocity value is converted into the flow rate value).

It is difficult to accurately attach the paired transducers 19 to the inclined lower portions 73 of the slider 71 of the unit 7. When they are incorrectly attached and shifted from their respective correct positions, cos$\theta$ is caused to have an error and the flow velocity of the liquid cannot be correctly measured.

As shown in FIG. 11, the electrical connector 32 is located at the other end of the cable 30 of the transducers 19, and the sensor unit 7 is thus connected to the pump drive unit 5 via the electrical connector 32.

In the external circulation system of this third embodiment, Ringer's solution in the container 3 (see FIG. 10) flows into the tube 16, flows through the branch pipe 15 and then flows together with blood into the centrifugal pump 2 through the inlet 14. Ringer's solution which has flowed into the centrifugal pump 2 is driven by the pump to flow together with blood outside the pump 2 through the outlet 13 and then into the inlet 11 of the artificial lung 1. Ringer's solution which has flowed into the artificial lung 1 flows together with blood from the blood chamber in the artificial lung 1 into the tube 16 through the outlet 17 which is attached to the lower portion of the artificial lung 1.

FIG. 11 is a block diagram showing the control circuit of the pump drive unit 5. This control circuit includes a CPU (or central processing unit) 330. The CPU 330 is connected to members 332-339 of the circuit through a data bus 331. The ROM 332 stores data programmed to variously control the pump drive unit 5 and data programmed to arithmetically calculate the flow rate of liquid in the tube 12 on the basis of various kinds of information supplied from the sensor unit 7. The RAM 333 is a memory for temporarily storing various kinds of data need to control the pump drive unit 5. The input port 334 serves to send the various kinds of information, which are supplied from the sensor 7 via the connectors 31, 32 through PORTs 1—1-1-5 (see FIG. 12), to the CPU 330.

Ultrasonic wave transmitter 335 and receiver 336 are connected to the connectors 31 and 32. An ultrasonic wave emitted from the UW (ultrasonic wave) transmitter 335 is emitted into the liquid in the tube 12 through one of the transducers 19. The ultrasonic wave in the liquid is reflected by reflectors (or blood cells or the like, for example) in the liquid, and is converted an electrical signal, and is received as reflected signals including those frequencies which have been shifted in proportion to the flow velocity of the liquid due to the Doppler effect. The UW receiver 336 serves to receive and to read only those signals which have been affected by the Doppler effect and to convert them into digital clock signals.

A counter 337 is connected to the UW receiver 336. The counter 337 counts, for every certain time period, the digital clock signals supplied from the UW receiver 336 to calculate the flow velocity of the liquid, and sends a result (or flow velocity data) thus calculated to the CPU 330 through the data bus 331. The CPU 330 calculates the correct flow rate of the liquid on the basis of the flow velocity data sent from the counter 337 and data relating to the diameter of the liquid-circulated passage and the value to correct the error of measurement sent from the sensor unit 7. Furthermore, the CPU 330 also displays the obtained correct flow rate on the display 338. The motor driver 339 drives the motor 4 for the centrifugal pump 2 responsive to a control signal supplied from the CPU 330.

Figure 12:
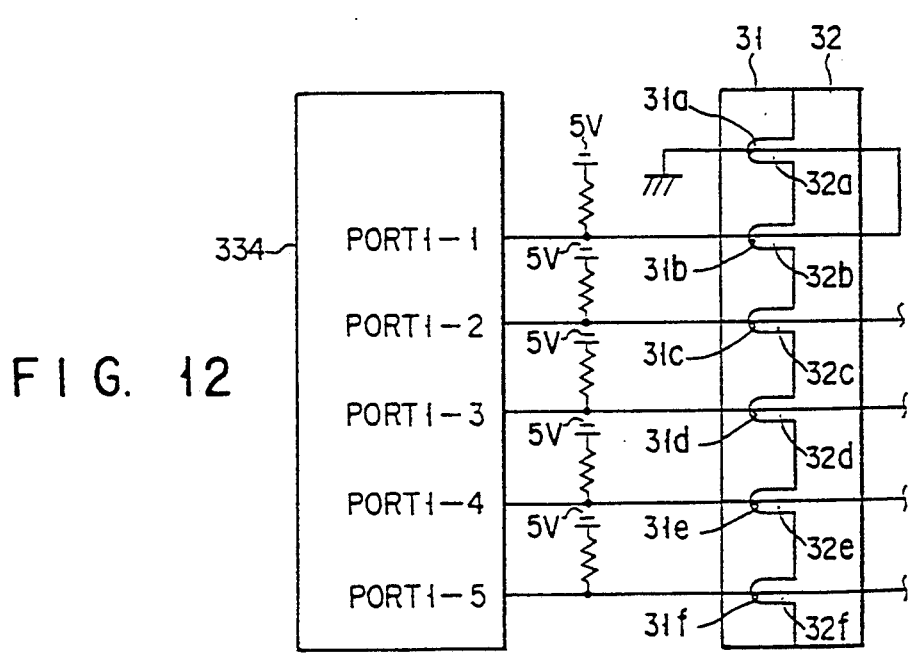
FIG. 12 is a wiring diagram showing electric connections between electrical connectors of a sensor unit and input ports.

As shown in FIG. 12, one electrical connector 31 has six sockets 31a-31f and the other electric connector 32 has six pins or plugs 32a-32f. When the pins 32a-32f are fitted into the sockets 31a-31f, the input port 334 of the pump drive unit 5 is electrically connected to the sensor unit 7. The pin 32a is electrically grounded and the other five pins 32b-32f serve as wiring pins. The number of wiring pins is not limited to five, but it may be plural.

Each of the wiring pins 32b-32f is connected or not connected to the grounded pin 31a responsive to the kind of the sensor unit 7 used and the value measured by the sensor and corrected, and these data are applied from the sensor unit 7. The wiring pins 32b-32f have the information of "0" (grounded) or "1" (opened). Their data are applied to their corresponding PORTs 1—1-1-5 of the input port 334.

Table 1 shows the information (or data relating to the kinds of sensor used and data relating to the values measured and corrected and the inner diameters of liquid-circulating passages used) which are applied from the sensor unit 7 to the PORTs 1—1-1-5 of the input port 334.

In the case of the wiring shown in FIG. 12, the grounded pin 32a is connected only to the wiring pin 32b and voltage signal applied to the PORT 1—1 is "0" while the voltage signal applied to each of the PORTs 1-2-1-5 is "1". As a result, signal data "0, 1, 1, 1, 1" shown at 1 (first line) in Table 1 is applied to the input port 334. This combination of signal data is temporarily stored in the RAM 333 and is used together with information supplied from the ROM 332 by the CPU 330 to arithmetically calculate the flow velocity V (or flow rate) of the liquid. When the signal data applied is "0, 1, 1, 1, 1" and the inner diameter of the tube 12 (or flow connector 18) is ⅜ inches, the value to be corrected becomes zero and this makes it unnecessary to correct the sensor unit 7, as indicated in Table 1. In the case of other combinations of signal data applied, as shown in Table 1, arithmetic calculations are conducted in the form of corrections 1-7 by the CPU 330. When all of the data applied to the PORTs 1—1-1-5 are "1", as shown at No. 17 in Table 1, the sensor unit 7 is not connected to the pump drive unit 5.

TABLE 1

| NO. | PI-1 | PI-2 | PI-3 | PI-4 | PI-5 | Inner Diameter of Passage | Corrected or not |
| --- | --- | --- | --- | --- | --- | --- | --- |
| 1 | 0 | 1 | 1 | 1 | 1 | 3/8 inch | not corrected |
| 2 | 0 | 1 | 0 | 1 | 1 | 3/8 inch | correction 1 |
| 3 | 0 | 1 | 1 | 0 | 1 | 3/8 inch | correction 2 |
| 4 | 0 | 1 | 0 | 0 | 1 | 3/8 inch | correction 3 |
| 5 | 0 | 1 | 1 | 1 | 0 | 3/8 inch | correction 4 |
| 6 | 0 | 1 | 0 | 1 | 0 | 3/8 inch | correction 5 |
| 7 | 0 | 1 | 1 | 0 | 0 | 3/8 inch | correction 6 |
| 8 | 0 | 1 | 0 | 0 | 0 | 3/8 inch | correction 7 |
| 9 | 1 | 0 | 1 | 1 | 1 | 1/4 inch | not corrected |
| 10 | 1 | 0 | 0 | 1 | 1 | 1/4 inch | correction 1 |
| 11 | 1 | 0 | 1 | 0 | 1 | 1/4 inch | correction 2 |
| 12 | 1 | 0 | 0 | 0 | 1 | 1/4 inch | correction 3 |
| 13 | 1 | 0 | 1 | 1 | 0 | 1/4 inch | correction 4 |
| 14 | 1 | 0 | 0 | 1 | 0 | 1/4 inch | correction 5 |
| 15 | 1 | 0 | 1 | 0 | 0 | 1/4 inch | correction 6 |
| 16 | 1 | 0 | 0 | 0 | 0 | 1/4 inch | correction 7 |
| 17 | 1 | 1 | 1 | 1 | 1 | | not connected |

According to this third embodiment, data relating to the inner diameter of the liquid-circulating passage used, and the value to be corrected, are supplied to the CPU 330 through the input port 334 when the sensor unit 7 is attached to the tube 12 through the connector 18 and the connector 32 is connected to the pump drive unit 5. When measurement is then started, the flow velocity data of the liquid in the tube 12 is applied from the sensor unit 7 to the counter 337. The CPU 330 calculates the flow rate of the liquid, using the data of the flow velocity and the inner diameter of the passage and the program data stored in the ROM 332, and then corrects the flow rate data to a correct value, using the information of the value to be corrected. The correct value thus obtained is displayed on the display 338.

While seeing the flow rate thus displayed on the display 338, the operator adjusts the dial 24 to control the flow rate of the liquid or blood then flowing through the liquid-circulating passage.

According to the above-described third embodiment, the operator can be informed of the correct flow rate automatically obtained by arithmetic calculation, without inputting any data relating to the inner diameter of the passage used and the value corrected into the CPU 330. This makes it necessary for the operator only to attach the sensor unit 7 to the flow connector 18 and to connect the electrical connector 32 to the connector 31. The selection of passage diameters and the calibration operation which were conventionally conducted can thus be made unnecessary in the case of the above-described embodiment, thereby enabling a quicker process to be achieved by an easier operation.

As mentioned above, according to the medical pump driving device of the present invention, the operator can easily recognize the set number of rotations of the motor (centrifugal pump). Therefore, the operator can safely operate the medical equipment such as the artificial lungs without taking care of the dial scale (set value) on the operation panel. Particularly, according to the present invention, there is merit in that the operation at the time of starting the pump can be easily performed.

Moreover, according to the device of the present invention, the motor can be intermittently driven, and the bubble in the liquid channel can be automatically and efficiently removed for short time. Therefore, at the time of the auxiliary circulation, the operator does not execute the complicated priming operation as in the prior art.

Furthermore, according to the device of the present invention, since the first mode in which the motor is driven at a constant speed and the second mode in which the motor is intermittently driven can be switched, the operator can freely select the constantly driving motor and the intermittently driving motor.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

According to the medical pump driving device of the present invention, various kinds of data can be automatically sent to the pump drive unit 5 to correct the measured flow rate, only by attaching the sensor unit 7 to the liquid-circulating passage and the pump drive unit. The operator can more quickly attach and detach the sensor unit to and from the liquid-circulating passage and the pump drive unit with an easier operation. Conventional troublesome work of selecting the inner diameter of the passage used and conducting a calibration operation can thus be made unnecessary, thereby enabling external and auxiliary circulations of liquid to be made ready in a shorter time.

What is claimed is:

1. A medical pump driving device comprising:
    a pump for transferring liquid in a liquid channel including a medical device;
    a motor for driving said pump;
    dial means for adjusting a number of rotations of said motor;
    an operating unit for operating said dial means;
    a first display for displaying the number of rotations of said motor set by operating said dial means by said operating unit when said pump is stopped;
    detecting means for detecting an actual number of rotations of said motor while said pump is being driven;
    a second display for displaying the actual number of rotations detected by said detecting means;
    a voltage variable device connected to a driving circuit of said motor and to said dial means;
    said operating unit operating said dial means based on the set number of rotations and the actual number of rotations respectively displayed on said first and second displays; and
    a driving voltage of said motor being changed by said voltage variable device so as to adjust the number of rotations of said motor.

2. The medical pump driving device according to claim 1, further comprising:
    calculating means for calculating a corrected value for correcting the set number of rotations based on the set number of rotations and the actual number of rotations;
    a storage unit for storing the corrected value calculated by said calculating means; and
    correcting means for correcting the set number of rotations of said motor based on said corrected value stored in said storage unit.

3. The medical pump driving device according to claim 1, further comprising:
    display changing means for changing the numbers respectively displayed on said first display [means-]and said second display.

4. The medical pump driving device according to claim 1, further comprising:
indicating means for indicating whether at least one of said first display and said second display is being used; and
wherein said first and second displays comprise a common display unit.

5. The medical pump driving device according to claim 1, further comprising:
control for controlling a drive of said motor means.

6. The medical pump driving device according to claim 1, further comprising an operation panel on which said dial means and said first and second display are mounted.

7. The medical pump driving device according to claim 1, wherein said detecting means includes a pulse generator and a counter. provide similar information or access to all the other applications in the same file wrapper.

8. The medical pump driving device according to claim 6, further comprising:
setting means for setting various set values to intermittently drive said motor;
set value storing means for storing a set value set by said setting means;
intermittent drive control means for intermittently driving said motor based on the set value stored in said set value storing means; and
a bubble expelling device communicating with said pump via said plurality of liquid passages to form a closed circuit, said closed circuit comprising said plurality of liquid passages, the pump, and said bubble expelling device, wherein said bubble expelling device permits a passage of a gas therethrough but does not permit a passage of a liquid therethrough; and
wherein said motor is intermittently driven to circulate the liquid through said closed circuit, said bubble expelling device expelling bubbles from the liquid flowing through said closed circuit.

9. The medical pump driving device according to claim 8, wherein said bubble expelling device comprises porous hollow fiber membranes communicating with said pump and which membranes permit a passage of a gas therethrough and do not permit a passage of a liquid therethrough.

10. The medical pump driving device according to claim 8, further comprising:
constant speed driving control means for controlling said motor to rotate at a constant speed; and
mode changing means for changing a first mode of said constant speed driving control means and a second mode of said intermittent drive control means.

11. The medical pump driving device according to claim 10, further comprising priority order setting means for setting said first mode prior to said second mode.

12. The medical pump driving device according to claim 8, further comprising:
a bubble detector for detecting a bubble in a liquid channel; and
wherein said intermittent drive control means controls an intermittent driving of said motor based on an output of said bubble detector.

13. The medical pump driving device according to claim 10, further comprising set value display means for displaying the set value stored in said set value storing means.

14. A medical pump driving device comprising:
a pump for circulating a liquid through a plurality of liquid passages connected to a medical device;
a motor for driving the pump;
a flow connector attached to one of said plurality of liquid passages, said flow connector having substantially a same diameter as a diameter of said one of said liquid passages;
a sensor unit having a flow velocity measuring sensor detachably attached to the flow connector for measuring a flow velocity of the liquid in the one liquid passage;
a first memory for storing in advance data relating to the diameter of the one liquid passage and data to correct a measuring error of the sensor unit for a particular medical device;
a second memory for temporarily storing, as data, the flow velocity of the liquid detected by the flow velocity measuring sensor;
electrical connectors for electrically coupling the flow velocity measuring sensor to the second memory;
calculating means for arithmetically calculating a flow rate of the liquid from data read from the first and second memories; and
means for controlling a flow rate of liquid in the plurality of liquid passages, responsive to the thus calculated flow rate of the liquid.

15. The pump driving device according to claim 14, further comprising:
holder means coupled to the sensor unit for holding the flow connector when the sensor unit is mounted on the flow connector.

16. The pump driving device according to claim 14, wherein the flow connector has two ends, and wherein each of both ends of the flow connector is conically shaped.

17. The pump driving device according to claim 16, wherein the flow connector is made of polycarbonate.

18. The pump driving device according to claim 14, wherein the flow velocity measuring sensor comprises a Doppler ultrasonic flowmeter having a pair of piezoelectric transducers.

* * * * *